US010506183B2

(12) United States Patent
Kuwabara et al.

(10) Patent No.: US 10,506,183 B2
(45) Date of Patent: *Dec. 10, 2019

(54) RADIOGRAPHIC IMAGING DEVICE, RADIOGRAPHIC IMAGING SYSTEM, CONTROL METHOD OF RADIOGRAPHIC IMAGING DEVICE AND PROGRAM STORAGE MEDIUM

(71) Applicant: FUJIFILM CORPORATION, Minato-ku, Tokyo (JP)

(72) Inventors: Takeshi Kuwabara, Kanagawa (JP); Yoshihiro Okada, Kanagawa (JP); Haruyasu Nakatsugawa, Kanagawa (JP); Naoyuki Nishino, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 192 days.

This patent is subject to a terminal disclaimer.

(21) Appl. No.: 15/694,095

(22) Filed: Sep. 1, 2017

(65) Prior Publication Data

US 2018/0013967 A1   Jan. 11, 2018

Related U.S. Application Data

(63) Continuation of application No. 14/525,219, filed on Oct. 28, 2014, now Pat. No. 9,787,919, which is a (Continued)

(30) Foreign Application Priority Data

May 30, 2012 (JP) .................................. 2012-123624
Nov. 16, 2012 (JP) .................................. 2012-252381

(51) Int. Cl.
*H04N 5/357* (2011.01)
*A61B 6/00* (2006.01)
(Continued)

(52) U.S. Cl.
CPC .......... *H04N 5/357* (2013.01); *A61B 6/4233* (2013.01); *A61B 6/4283* (2013.01); *A61B 6/44* (2013.01);
(Continued)

(58) Field of Classification Search
CPC .......... H04N 5/357; H04N 5/32; H04N 5/369; A61B 6/4233; A61B 6/4283; A61B 6/44;
(Continued)

(56) References Cited

U.S. PATENT DOCUMENTS 9,787,919 B2 *  10/2017  Kuwabara ................ H04N 5/32
2003/0086523 A1   5/2003  Tashiro et al.
(Continued)

FOREIGN PATENT DOCUMENTS

CN    102780857 A    11/2012
JP    2001-160926 A    6/2001
(Continued)

OTHER PUBLICATIONS

English language translation of the following: Office action dated Jan. 29, 2019 from the JPO in a Japanese patent application No. 2017-254765 corresponding to the instant patent application. This office action translation is submitted now in order to supplement the understanding of the cited reference which is being disclosed in the instant Information Disclosure Statement.
(Continued)

*Primary Examiner* — Courtney D Thomas
(74) *Attorney, Agent, or Firm* — SOLARIS Intellectual Property Group, PLLC

(57) ABSTRACT

A radiographic imaging device includes: a radiation detector including plural pixels, each including a sensor portion and a switching element; a detection unit that detects a radiation irradiation start if an electrical signal caused by charges generated in the sensor portion satisfies a specific irradiation
(Continued)

detection condition, and/or if an electrical signal caused by charges generated in a radiation sensor portion that is different from the sensor portion satisfies a specific irradiation detection condition; and a control unit that determines whether or not noise caused by external disturbance has occurred after the detection unit has detected the radiation irradiation start, and if the noise has occurred, that stops a current operation of the radiation detector, and causes the detection unit to perform detection.

23 Claims, 20 Drawing Sheets

Related U.S. Application Data continuation of application No. PCT/JP2012/081296, filed on Dec. 3, 2012.

(51) Int. Cl.
| | |
|---|---|
| H04N 5/369 | (2011.01) |
| G01N 23/04 | (2018.01) |
| G01T 1/17 | (2006.01) |
| G01T 1/20 | (2006.01) |
| H04N 5/32 | (2006.01) |

(52) U.S. Cl.
CPC .......... *A61B 6/5258* (2013.01); *A61B 6/5264* (2013.01); *A61B 6/542* (2013.01); *G01N 23/04* (2013.01); *G01T 1/17* (2013.01); *G01T 1/20* (2013.01); *H04N 5/32* (2013.01); *H04N 5/369* (2013.01)

(58) Field of Classification Search
CPC ..... A61B 6/5258; A61B 6/5264; A61B 6/542; G01N 23/04; G01T 1/17; G01T 1/20
USPC .......................................... 378/62, 98.8, 114
See application file for complete search history.

(56) References Cited

U.S. PATENT DOCUMENTS

| | | |
|---|---|---|
| 2006/0215049 A1 | 9/2006 | Sandini et al. |
| 2011/0215250 A1 | 9/2011 | Ohta et al. |
| 2011/0221945 A1 | 9/2011 | Kurokawa et al. |
| 2012/0001080 A1 | 1/2012 | Okada |
| 2012/0091353 A1 | 4/2012 | Enomoto |
| 2012/0114099 A1 | 5/2012 | Yoshida |
| 2012/0132821 A1 | 5/2012 | Kuwabara |
| 2012/0288061 A1 | 11/2012 | Okada |
| 2013/0099128 A1 | 4/2013 | Shikino et al. |

FOREIGN PATENT DOCUMENTS

| | | | |
|---|---|---|---|
| JP | 2003-126072 A | | 5/2003 |
| JP | 2004-24683 A | | 1/2004 |
| JP | 2005-006790 A | | 1/2005 |
| JP | 2005-006791 A | | 1/2005 |
| JP | 2006-246961 A | | 9/2006 |
| JP | 2006-322888 A | | 11/2006 |
| JP | 2006322888 A | * | 11/2006 |
| JP | 2006-333898 A | | 12/2006 |
| JP | 2007-105112 A | | 4/2007 |
| JP | 2010-217141 A | | 9/2010 |
| JP | 2010-268171 A | | 11/2010 |
| JP | 2011-200630 A | | 10/2011 |
| JP | 2011-226902 A | | 11/2011 |
| JP | 2012-074817 A | | 4/2012 |
| JP | 2012-75077 A | | 4/2012 |
| JP | 2012-85795 A | | 5/2012 |
| JP | 2012-095967 A | | 5/2012 |
| JP | 2013-106919 A | | 6/2013 |

OTHER PUBLICATIONS

Office Action dated Mar. 16, 2018, issued by the EPO in corresponding EP Patent Application No. EP12878147.3.
Written Opinion of the ISA issued in International Application No. PCT/JP2012/081296 dated Jan. 29, 2013.
International Search Report issued in International Application No. PCT/JP2012/081296 dated Jan. 29, 2013.
Asahi Glass Co., Ltd. "AGC Develops World's Thinnest Sheet Float Glass at Just 0.1 MM" <http://www.agc.com/news/2011/0516.pdf>.
Notice of Reasons for Rejection issued in Corresponding Japanese Patent Application No. 2012-252381.
Extended European Search Report dated Dec. 15, 2015, issued in the corresponding European Patent Application No. 12878147.3.
Communication pursuant to Article 94(3) EPC dated Nov. 10, 2016, issued in the corresponding European Patent Application No. 12878147.3.
English language translation of the following: Office action dated Jan. 5, 2017 from the SIPO in a Chinese patent application No. 201280073389.1 corresponding to the instant patent application. This office action translation is submitted now in order to supplement the understanding of the cited reference which is being disclosed in the instant Information Disclosure Statement.
Communication pursuant to Article 94(3) EPC dated Jul. 19, 2017, issued in corresponding EP Patent Application No. 12878147.3.
English language translation of the following: Office action dated Jul. 18, 2017 from the SIPO in a Chinese patent application No. 201280073389.1 corresponding to the instant patent application. This office action translation is submitted now in order to supplement the understanding of the cited reference which is being disclosed in the instant Information Disclosure Statement.
English language translation of the following: Office action dated Aug. 8, 2017 from the JPO in a Japanese patent application No. 2016-206343 corresponding to the instant patent application. This office action translation is submitted now in order to supplement the understanding of the cited reference which is being disclosed in the instant Information Disclosure Statement.
English language translation of the following: Office action dated Oct. 1, 2019 from the JPO in a Japanese patent application No. 2017-254765 corresponding to the instant patent application. This office action is submitted now in order to supplement the understanding of the cited reference which is being disclosed in the instant Information Disclosure Statement.

* cited by examiner

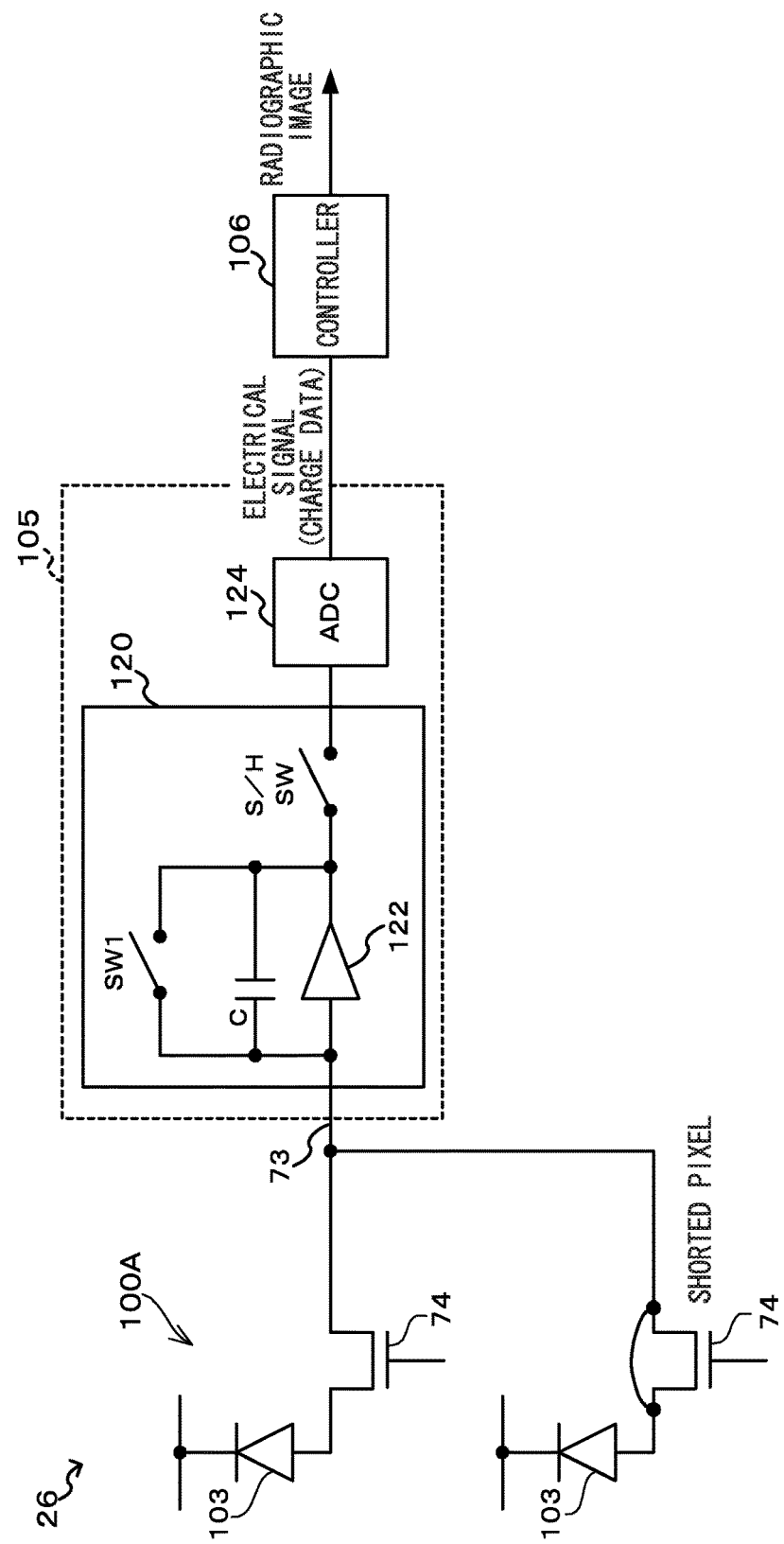

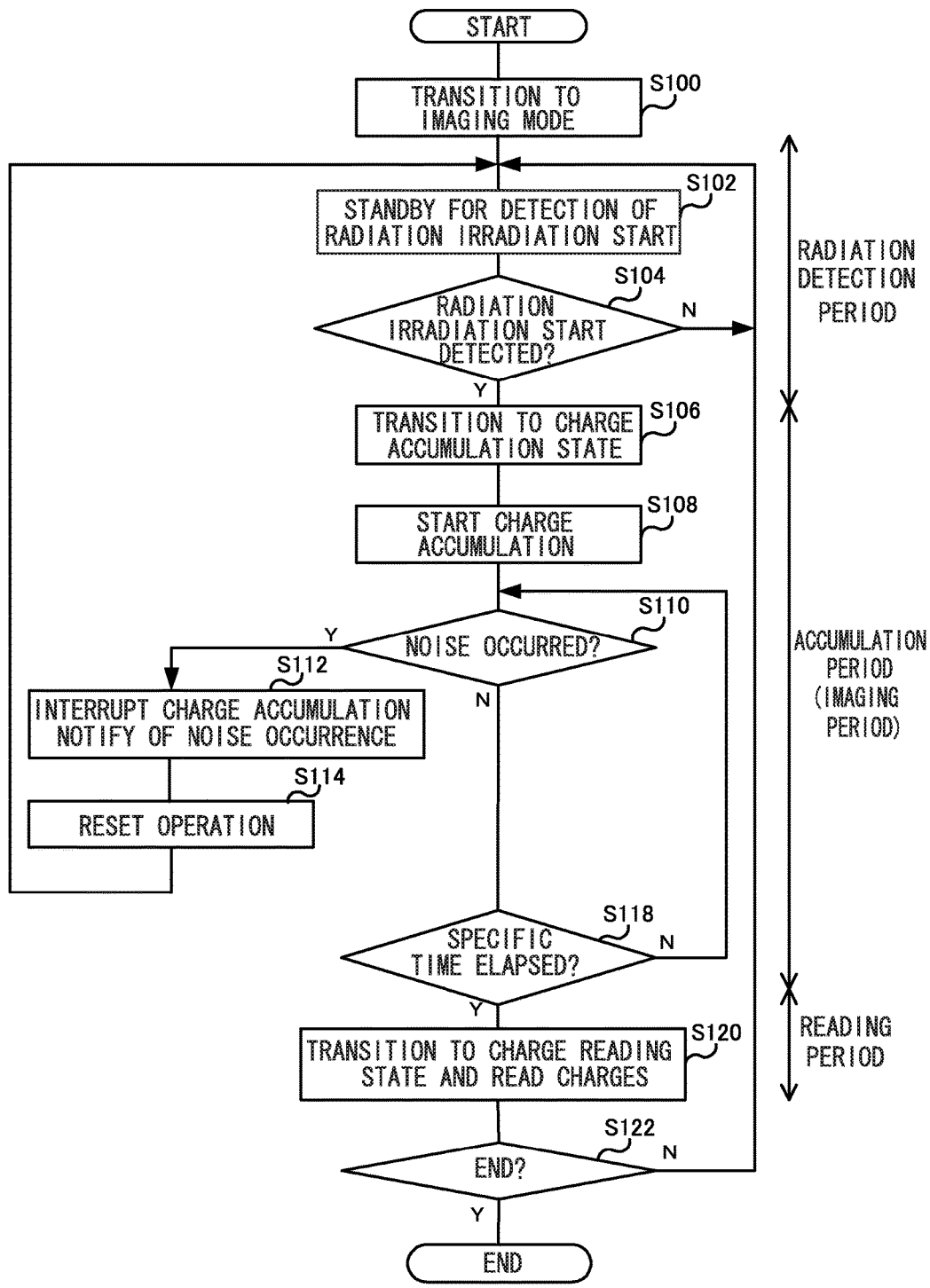

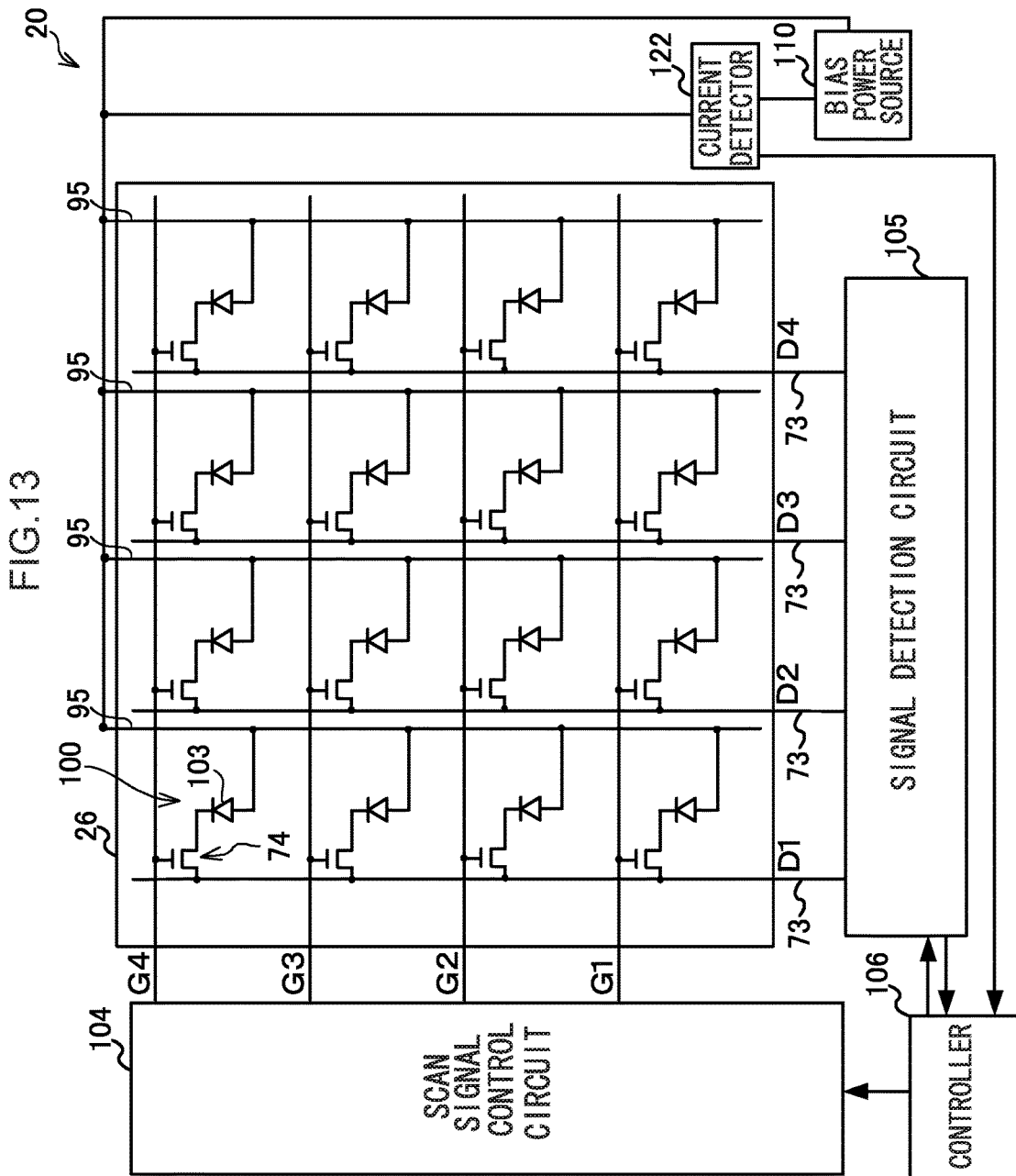

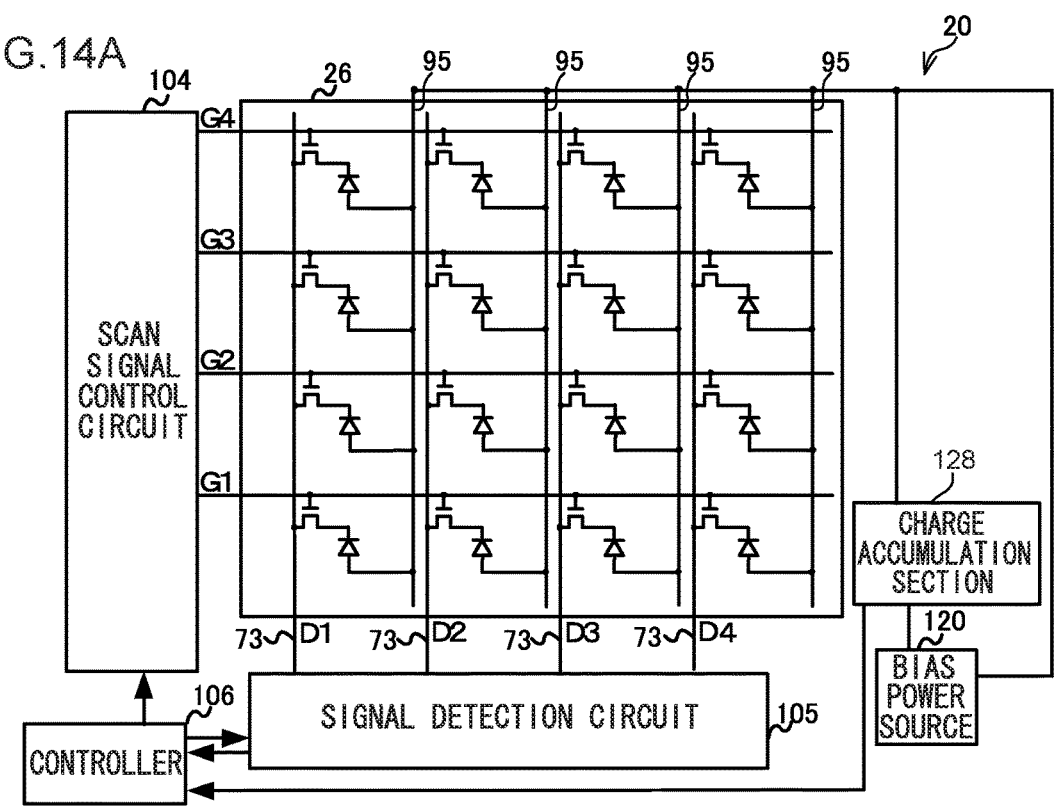
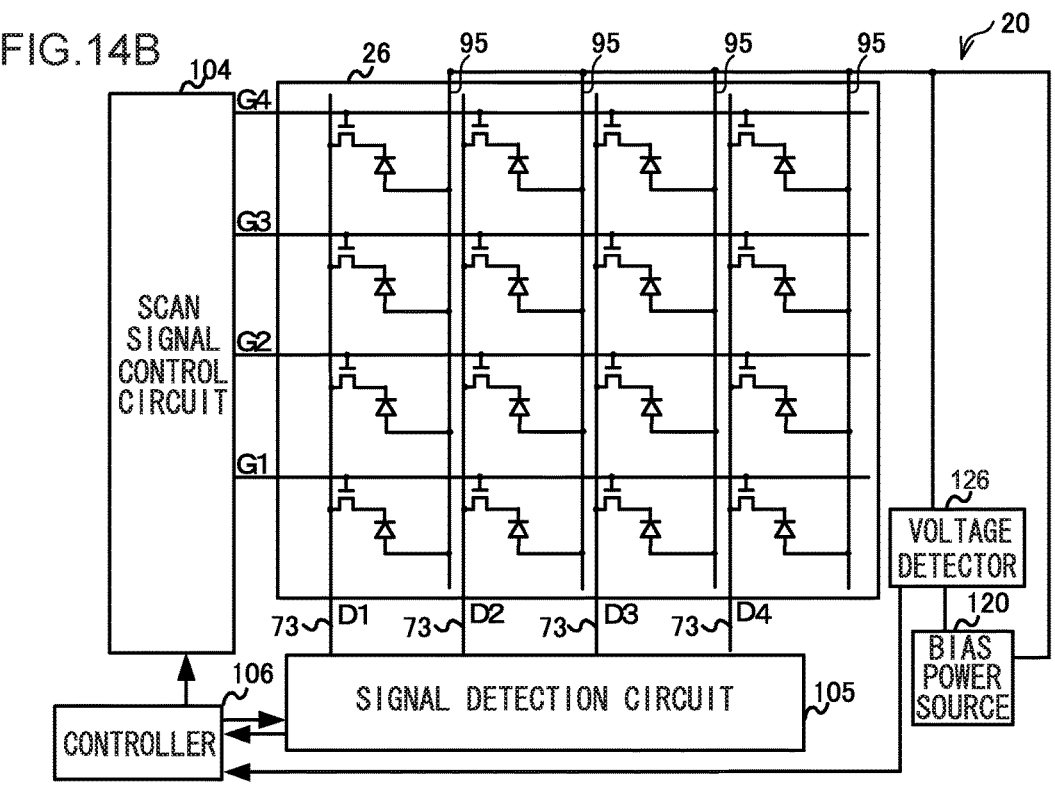

RADIATION X 172
170
174 174 174 174 174

170(26) (BOTTOM FACE)

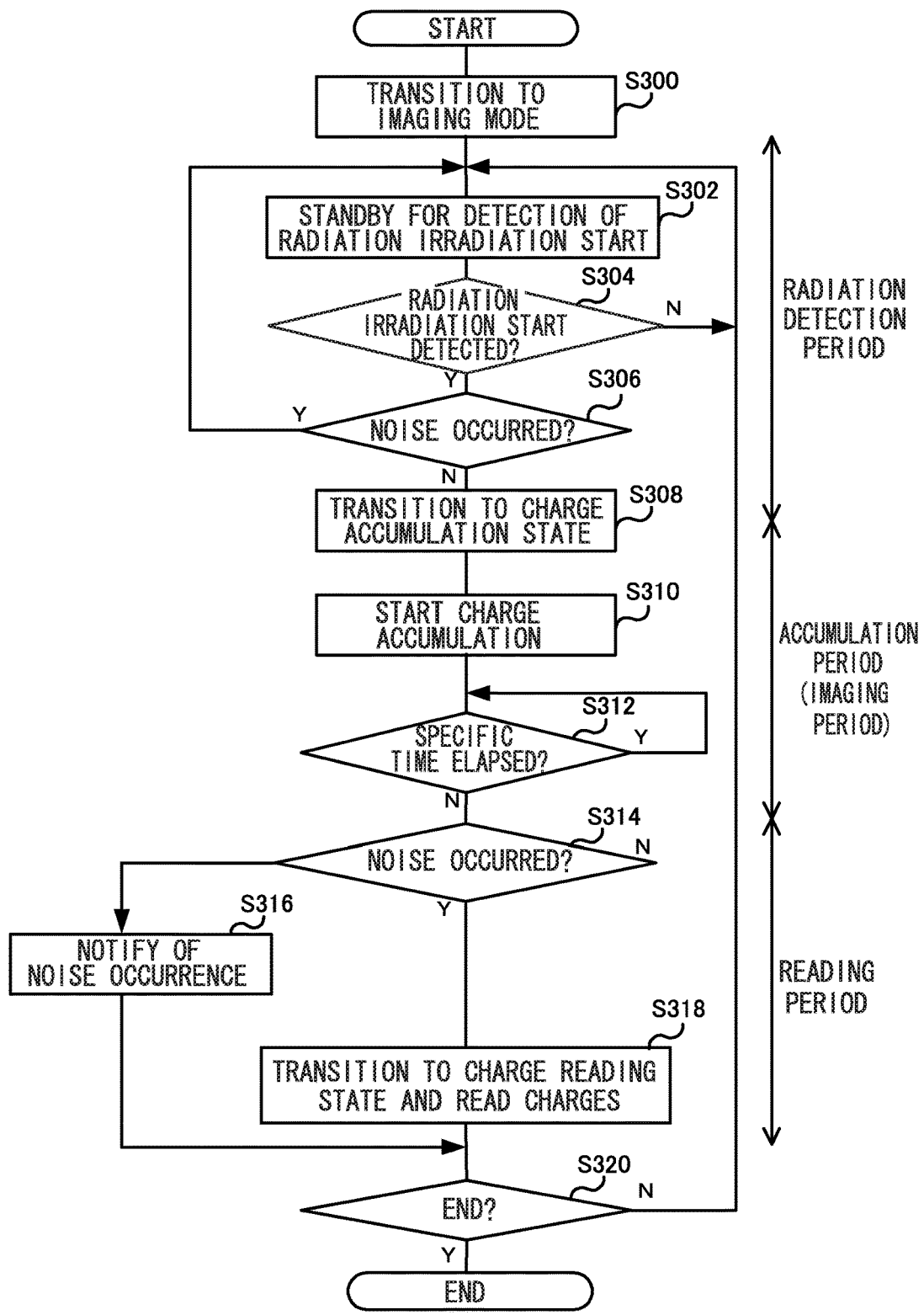

RADIOGRAPHIC IMAGING DEVICE, RADIOGRAPHIC IMAGING SYSTEM, CONTROL METHOD OF RADIOGRAPHIC IMAGING DEVICE AND PROGRAM STORAGE MEDIUM

CROSS-REFERENCE TO RELATED APPLICATIONS

This application is a continuation application of application Ser. No. 14/525,219, filed on Oct. 28, 2014, which is a continuation application of International Application No. PCT/JP2012/081296, filed on Dec. 3, 2012, the entire contents of these applications are incorporated herein by reference in their entirety. Further, this application claims priority from Japanese Patent Applications No. 2012-123624, filed on May 30, 2012, and No. 2012-252381, filed on Nov. 16, 2012, the disclosures of which are incorporated by reference herein in their entirety.

BACKGROUND OF THE INVENTION

Field of the Invention

The present invention relates to a radiographic imaging device, a radiographic imaging system, a control program storage medium for a radiographic imaging device, and a control method for a radiographic imaging device. In particular, the present invention relates to a radiographic imaging device, a radiographic imaging system, a control program storage medium for a radiographic imaging device, and a control method for radiographic imaging device that capture radiographic images for medical purposes.

Related Art

Radiographic imaging devices are known that perform radiographic imaging for medical diagnostic purposes. Such radiographic imaging devices detect radiation that has been irradiated from a radiation irradiation device and has passed through a subject to capture radiographic images. The radiographic imaging devices perform radiographic imaging by collecting and reading charges generated according to irradiated radiation.

Such known radiographic imaging devices include an irradiation detector provided with sensor portions, such as photoelectric conversion elements that generate charges upon irradiation with radiation or illumination with light converted from radiation, and switching elements that read the charges generated in the sensor portion. The irradiation detector detects that radiation irradiation has started (that radiographic imaging has started) or the like based on the charges read from the switching elements.

In such radiographic imaging devices provided with an irradiation detector that detects radiographic imaging start, the irradiation detector may falsely detects that radiation irradiation has started due to charges generated in the sensor portions resulting from noise caused by external disturbance such as impacts or electromagnetic waves.

Technology such as the following exists to prevent false detection. For example, Japanese Patent Application Laid-Open (JP-A) No. 2010-268171 describes technology for a radiographic imaging device that detects radiation irradiation start based on the value of a current flowing in a bias line, to prevent false detection of radiation irradiation start at the rise of a voltage value overlaid on a current flowing in a bias line due to noise when switching between an ON voltage and an OFF voltage that are applied to a switching element.

JP-A No. 2006-246961 describes technology to enable accurate detection of an imaging start timing in an X-ray imaging device regardless of whether the X-ray irradiation cycles according to a half wave rectified waveform of an AC power source voltage, or is constant according to a voltage waveform of a completely DC voltage obtained by a high frequency inverter method, while preventing false operation due to noise.

In the above technologies, there may be cases in which it takes time to detect the occurrence of noise in the technology described above, and the detection cannot be performed in real time. There are accordingly cases in which it takes time to determine that the irradiation detector has falsely detected radiation irradiation start, and there may be cases in which detection cannot be made in this interval even if radiation for radiographic imaging has been applied. There is accordingly demand to detect the occurrence of noise in real time, without any delay, in a case in which noise due to an external disturbance, particularly an impact (vibration) has occurred, and for this to be reflected in the operation of a radiation detector.

SUMMARY

The present invention provides a radiographic imaging device, a radiographic imaging system, a control program for a radiographic imaging device, and a control method for a radiographic imaging device that enable detection of the occurrence of noise and control of an imaging operation without any delay in cases in which noise caused by external disturbance occurs.

A first aspect of the present invention is a radiographic imaging device including: a radiation detector including plural pixels, each including a sensor portion that generates charges according to an amount of irradiated radiation and accumulates the generated charges, and a switching element that reads the charges from the sensor portion based on a control signal and outputs electrical signals according to the charges into a signal line; a detection unit that performs a detection operation that detects a radiation irradiation start in at least one of a case in which an electrical signal caused by charges generated in the sensor portion satisfies a specific irradiation detection condition, or a case in which an electrical signal caused by charges generated in a radiation sensor portion that is different from the sensor portion satisfies a specific irradiation detection condition; and a control unit that causes the radiation detector to perform a first operation after the detection means has detected the radiation irradiation start, determines whether or not noise caused by external disturbance has occurred during performance of the first operation, and in a case in which the noise has occurred, that causes the radiation detector to stop the first operation, and causes the detection unit to perform the detection operation.

A second aspect of the present invention is the radiographic imaging device of the first aspect, wherein the first operation may be an accumulation operation in which the sensor portions accumulate charges.

A third aspect of the present invention is the radiographic imaging device of the first or second aspect, after the detection unit has detected radiation irradiation start and before performing the first operation, the control unit may determine whether or not the noise has occurred, and causes the sensor portions to start the first operation in a case in which the noise has not occurred.

A fourth aspect of the present invention is the above aspect, wherein the control unit may detect changes in an electrical signal caused by charges generated in the sensor portions, and determine whether or not the noise has occurred based on change with time of the electrical signal.

A fifth aspect of the present invention is the radiographic imaging device of the fourth aspect, wherein a shorted pixel in which the switching element has been shorted may be included in the plural pixels; and the control unit may determine whether or not the noise has occurred based on change with time of an electrical signal caused by charges generated in the sensor portion of the shorted pixel.

A sixth aspect of the present invention is the radiographic imaging device of either the fourth aspect or the fifth aspect, further including a common electrode line that supplies a bias voltage to the sensor portions; wherein the control unit may determine whether or not the noise has occurred based on change with time of an electrical signal flowing in the common electrode line caused by charges generated in the sensor portions.

A seventh aspect of the present invention is the radiographic imaging device of any one of the fourth aspect to the sixth aspect, further including a radiation sensor portion provided at least one of internally or externally to the radiation detector; wherein the control unit may determine whether or not the noise has occurred based on change with time of an electrical signal caused by charges generated in the radiation sensor portion.

An eighth aspect of the present invention is any one of the fourth aspect to the seventh aspect, wherein the control unit may detect changes in an electrical signal in a period from after the detection unit has detected radiation irradiation start until radiation irradiation stops, and determine whether or not the noise has occurred based on change with time of the electrical signal.

A ninth aspect of the present invention is any one of the fourth aspect to the eighth aspect, wherein the control unit may determine whether or not the noise has occurred based on change with time of at least one of polarity of charges, or the amplitude of a waveform representing change with time of a charge amount, according to an electrical signal.

A tenth aspect of the present invention is the radiographic imaging device of any one of the fourth aspect to the ninth aspect, wherein an electrical signal with which the detection unit detects radiation irradiation start, and an electrical signal with which the control unit determines whether or not the noise has occurred, may be different types of electrical signals from each other.

An eleventh aspect of the present invention is the above aspects, wherein the control unit may determine whether or not the noise has occurred using at least one of a predetermined criterion for each specific region where the pixels are provided, or a predetermined criterion for each of the signal lines.

A twelfth aspect of the present invention is the radiographic imaging device of the above aspects, further including a detection portion that detects at least one of an impact imparted to the radiation detector from outside, or electromagnetic waves; wherein the control unit may determine whether or not the noise has occurred based on a detection result of the detection portion.

A thirteenth aspect of the present invention is the radiographic imaging device of the above aspects, wherein a shorted pixel in which the switching element has been shorted may be included in the plural pixels; and the detection unit may detect the radiation irradiation start in a case in which an electrical signal caused by charges generated in the sensor portion of the shorted pixel satisfies a specific irradiation detection condition.

A fourteenth aspect of the present invention is the radiographic imaging device of the above aspects, further including a common electrode line that supplies a bias voltage to the sensor portions; wherein the detection unit may detect the radiation irradiation start in a case in which an electrical signal flowing in the common electrode line caused by charges generated in the sensor portions satisfies a specific irradiation detection condition.

A fifteenth aspect of the present invention is the radiographic imaging device of the above aspects, further including a radiation sensor portion provided at least one of internally or externally to the radiation detector; wherein the detection unit may detect as radiation irradiation start in a case in which an electrical signal caused by charges generated in the radiation sensor portion satisfies a specific irradiation detection condition.

A sixteenth aspect of the present invention is the radiographic imaging device of the above aspects, wherein the first operation may be a reading operation in which charges are read from the sensor portions by the switching elements.

A seventeenth aspect of the present invention is the above aspects, wherein the control unit may control a notification unit to provide notification in the case in which noise has occurred.

An eighteenth aspect of the present invention is a radiographic imaging system including an irradiation device that irradiates radiation; and the radiographic imaging device of the present invention that captures a radiographic image according to radiation irradiated from the irradiation device.

A nineteenth aspect of the present invention is a non-transitory storage medium storing a control program that causes a radiographic imaging device to perform control processing, the radiographic imaging device including a radiation detector including plural pixels, each including a sensor portion that generates charges according to an amount of irradiated radiation and accumulates the generated charges, and a switching element that reads the charges from the sensor portion based on a control signal and outputs electrical signals according to the charges into a signal line, the control processing including: detecting a radiation irradiation start by at least one of: (a) detecting an electrical signal caused by charges generated in the sensor portion satisfying a specific irradiation detection condition, or (b) detecting an electrical signal caused by charges generated in a radiation sensor portion that is different from the sensor portion satisfying a specific irradiation detection condition; causing the radiation detector to perform a first operation after the detection means has detected the radiation irradiation start; determining whether or not noise caused by external disturbance has occurred during performance of the first operation; and in a case in which the noise has occurred, stopping the first operation of the radiation detector and performing again the detection of radiation irradiation start.

A twentieth aspect of the present invention is a control method for a radiographic imaging device including a radiation detector including plural pixels, each including a sensor portion that generates charges according to an amount of irradiated radiation and accumulates the generated charges, and a switching element that reads the charges from the sensor portion based on a control signal and outputs electrical signals according to the charges into a signal line, the radiographic imaging device control method including: detecting a radiation irradiation start by at least one of: (a)

detecting an electrical signal caused by charges generated in the sensor portion satisfying a specific irradiation detection condition, or (b) detecting an electrical signal caused by charges generated in a radiation sensor portion that is different to the sensor portion satisfying a specific irradiation detection condition; causing the radiation detector to perform a first operation after the detection means has detected the radiation irradiation start; determining whether or not noise caused by external disturbance has occurred during performance of the first operation; and in a case in which the noise has occurred, stopping the first operation of the radiation detector and performing again the detection of radiation irradiation start.

The present invention exhibits the effect of enabling detection of the occurrence of noise and allowing control of an imaging operation without any delay in cases in which noise caused by external disturbance occurs.

BRIEF DESCRIPTION OF THE DRAWINGS

FIG. 6 is a schematic configuration diagram illustrating an example of a schematic configuration of a signal detection circuit of a radiographic imaging device according to the first exemplary embodiment.

FIG. 9 is a flowchart illustrating an example of a flow of operation during radiographic imaging according to the first exemplary embodiment.

FIG. 13 is a configuration diagram illustrating an example of an overall configuration of an electronic cassette according to a second exemplary embodiment.

FIG. 14A is a configuration diagram illustrating an example of an overall configuration of an electronic cassette according to another embodiment.

FIG. 14B is a configuration diagram illustrating an example of an overall configuration of an electronic cassette according to another embodiment.

FIG. 21 is a flowchart illustrating an example of a flow of operation in radiographic imaging according to a sixth exemplary embodiment.

DETAILED DESCRIPTION

Figure 1:
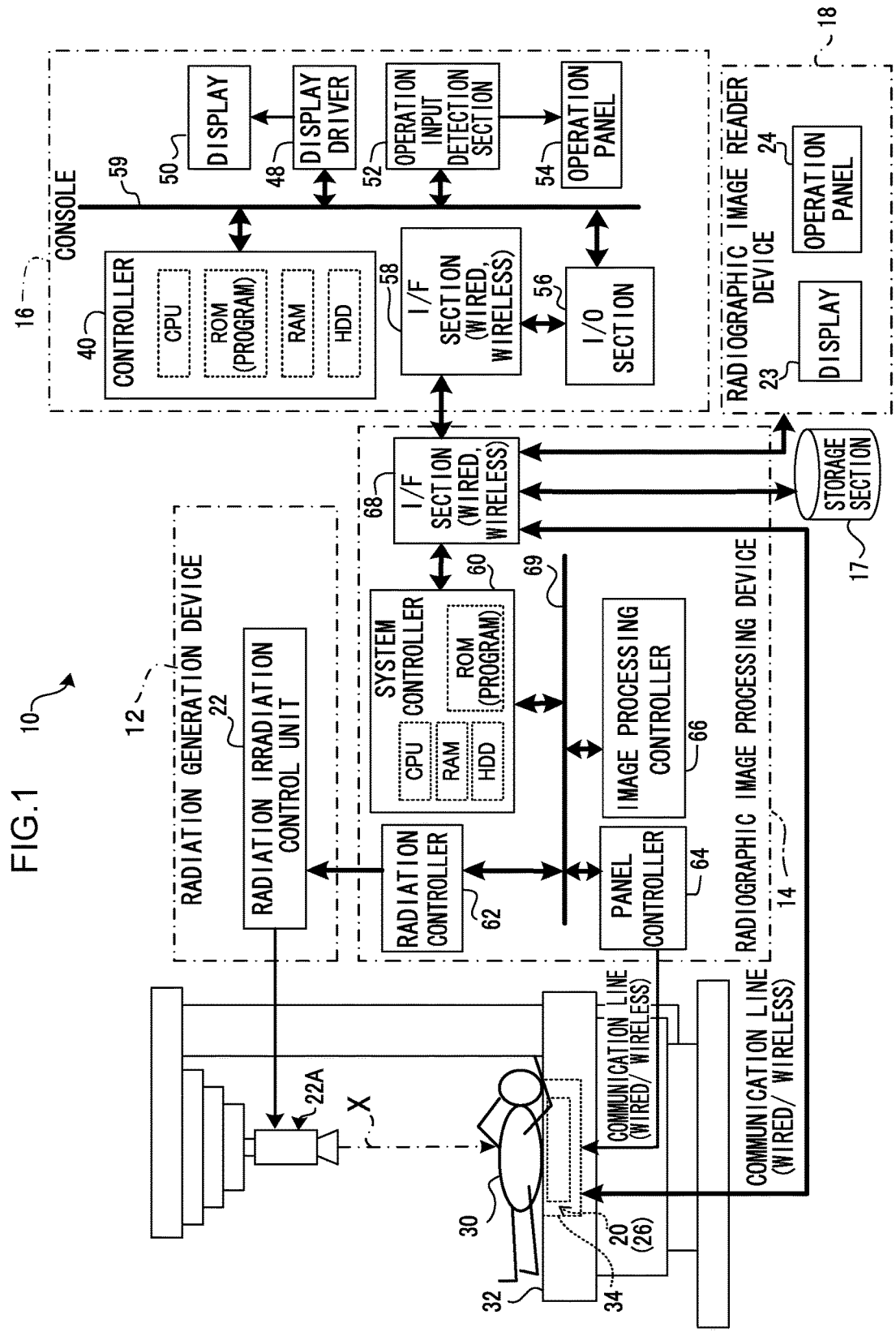
FIG. 1 is a schematic diagram illustrating a schematic configuration of an example of a radiographic imaging system according to a first exemplary embodiment.

The present invention may be applied to the following methods to detect the start of radiation irradiation (the start of imaging).

(1) Pixels freely selected from pixels (a two dimensional array) for radiographic imaging are used as dedicated pixels for radiation detection. In such cases, the radiographic imaging pixels and the radiation detection pixels have a same form.

(2) Pixels freely selected from pixels (a two dimensional array) for radiographic imaging are configured to have structures also capable of radiation detection. Namely, some of the pixels are used both for radiographic imaging and for radiation detection. For example, the sensor portion of each selected pixel is divided into two, and the sensor portion is selectively used for performing radiographic imaging, or for performing radiation detection. Alternatively, additional TFT switches may be disposed to the selected pixels, and radiation may be detected based on leak current of the additionally disposed TFT switches.

(3) Dedicated radiation detection sensors are arbitrarily disposed between pixels (for example in inter-pixel gaps) for radiographic imaging (a two dimensional array).

In methods (2) and (3), only selected pixels (selected gaps) may have such structure in a radiation detector employing these methods. Alternatively, the structure of the sensor portions and the TFT switches may have a repeating pattern, with connections made so as to only extract charges from the selected pixels.

(4) A separate detection unit is provided, without modifying radiographic imaging pixels (a two dimensional array) or the gaps therebetween. Examples for the detection methods include bias current detection, gate current detection, leak current detection, or the like in the radiation detector.

(5) A radiographic imaging controller may be used without providing a separate detection unit, and without modifying radiographic imaging pixels (a two dimensional array) or the gaps therebetween. Examples for the detection method include leak current detection or the like.

All of the methods (1) to (5) are compatible with cases in which a sensor is provided within a radiation detector that generate charges (electrical signals) according to the irradiated amount of radiation. There is no limitation thereto, and a sensor may be provided externally to a radiation detector as in (6) below. Sensors within a radiation detector, and sensors external to a radiation detector, are referred to collectively as radiation sensors.

(6) A radiation detection sensor is provided externally to a radiation detector. For example, a radiation detection sensor is provided on a bottom face of a radiation detector that is not irradiated with radiation.

In all of the above methods (1) to (6), configuration may be made such that radiation is detected in cases in which the gate of a TFT switch is in an ON state, or such that radiation is detected in cases in which the gate is in an OFF state.

Detailed explanation follows regarding exemplary embodiments in which the present invention is applied to a typical detection method among the above methods for detecting the start of radiation irradiation (the start of imaging).

First Exemplary Embodiment

Explanation follows regarding an example of the present exemplary embodiment, with reference to the drawings.

Explanation first follows regarding an outline configuration of an overall radiographic imaging system provided with a radiographic image processing device of the present exemplary embodiment. FIG. 1 illustrates a schematic configuration diagram of an outline overall configuration of an example of a radiographic imaging system of the present exemplary embodiment. In a radiographic imaging system 10 of the present exemplary embodiment, an electronic cassette 20 itself has a function to detect radiation irradiation start (imaging start).

The radiographic imaging system 10 of the present exemplary embodiment includes a function to perform radiographic imaging under operation by a doctor, radiologist, or the like, based on instructions (an imaging menu) input from an external system (such as a Radiology Information System (RIS)) through a console 16.

The radiographic imaging system 10 of the present exemplary embodiment includes a function of displaying captured radiographic images on a display 50 of the console 16 or a radiographic image reader 18 for a doctor, radiologist, or the like to read radiographic images.

The radiographic imaging system 10 of the present exemplary embodiment includes a radiation generator 12, a radiographic image processing device 14, a console 16, a storage section 17, a radiographic image reader 18, and the electronic cassette 20.

The radiation generator 12 includes a radiation irradiation control unit 22. The radiation irradiation control unit 22 includes a function to irradiate radiation X from a radiation irradiation source 22A onto an imaging target site of a subject 30 on an imaging table 32, under control of a radiation controller 62 of the radiographic image processing device 14.

The radiation X that has passed through the subject 30 is irradiated onto the electronic cassette 20 held by a holder 34 inside the imaging table 32. The electronic cassette 20 includes functions to generate charges according to the amount of radiation X passing through the subject 30, and to generate and output image data representing a radiographic image based on the generated charge amounts. The electronic cassette 20 of the present exemplary embodiment includes a radiation detector 26.

In the present exemplary embodiment, image data representing a radiographic image output by the electronic cassette 20 is input to the console 16 through the radiographic image processing device 14. The console 16 of the present exemplary embodiment includes a function to control the radiation generator 12 and the electronic cassette 20 using an imaging menu, various data and the like, acquired from an external system (RIS) through wireless communication (a Local Area Network (LAN)) or the like. The console 16 of the present exemplary embodiment includes a function to perform transmission and reception of various data, including image data of radiographic images, to and from the radiographic image processing device 14, and a function to perform transmission and reception of various data to and from the electronic cassette 20.

The console 16 of the present exemplary embodiment is a server computer. The console 16 includes a controller 40, a display driver 48, the display 50, an operation input detection section 52, an operation panel 54, an I/O section 56, and an I/F section 58.

The controller 40 includes a function to control overall operation of the console 16, and includes a CPU, ROM, RAM, and a HDD. The CPU includes a function to control the overall operation of the console 16, and various programs and the like, including a control program used by the CPU, are pre-stored in the ROM. The RAM includes a function to temporarily store various data, and the Hard Disk Drive (HDD) includes a function to store and retain various data.

The display driver 48 includes a function to control display of various data on the display 50. The display 50 of the present exemplary embodiment includes a function to display an imaging menu, captured radiographic images, and the like. The operation input detection section 52 includes a function to detect the operation state of the operation panel 54. The operation panel 54 is configured to allow input of operation instructions relating to radiographic imaging by a doctor, radiologist, or the like. Examples of the operation panel 54 according to the present exemplary embodiment include a touch panel, a touch pen, plural keys, a mouse, and the like. Combination with the display 50 may be achieved by configuration as a touch panel.

The I/O section 56 and the I/F section 58 include functions to perform transmission and reception of various data between the radiographic image processing device 14 and the radiation generator 12, and to perform transmission and reception of various data such as image data to and from the electronic cassette 20, through wireless communication.

The controller 40, the display driver 48, the operation input detection section 52, and the I/O section 56 are connected together through a bus 59, such as a system bus, a control bus, or the like, such that data and the like can be mutually exchanged therebetween. The controller 40 is accordingly capable of controlling display of various data on the display 50 through the display driver 48, and of controlling transmission and reception of various data to and from the radiation generator 12 and the electronic cassette 20 through the I/F section 58.

The radiographic image processing device 14 of the present exemplary embodiment includes a function to control the radiation generator 12 and the electronic cassette 20 according to instructions from the console 16. The radiographic image processing device 14 includes functions to store radiographic images received from the electronic cassette 20 in the storage section 17, and to control display on the display 50 of the console 16 and on the radiographic image reader 18.

The radiographic image processing device 14 of the present exemplary embodiment includes a system controller 60, a radiation controller 62, a panel controller 64, an image processing controller 66, and an I/F section 68.

The system controller 60 includes a function to control the overall radiographic image processing device 14, and includes a function to control the radiographic imaging system 10. The system controller 60 includes a CPU, ROM, RAM, and a HDD. The CPU includes a function to control overall operation of the radiographic image processing device 14 and to control operation of the radiographic imaging system 10. Various programs, such as a control program used by the CPU and the like, are pre-stored on the ROM. The RAM includes a function to temporarily store various data. The HDD includes a function to store and hold various data. The radiation controller 62 includes a function to control the radiation irradiation control unit 22 of the radiation generator 12 according to instruction of the console 16. The panel controller 64 includes a function to receive data from the electronic cassette 20, either wirelessly or by wire. The image processing controller 66 includes a function to perform various types of image processing on radiographic images.

The system controller 60, the radiation controller 62, the panel controller 64, and the image processing controller 66 are mutually connected together through a bus 69, such as a system bus, a control bus, or the like, such that data and the like can be mutually exchanged therebetween.

The storage section 17 of the present exemplary embodiment includes a function to store captured radiographic images and data related to such radiographic images. An example of the storage section 17 is a HDD or the like.

The radiographic image reader 18 of the present exemplary embodiment is a device including a function to allow a viewer to read the captured radiographic images. The radiographic image reader 18 is not particularly limited, and examples thereof include a reader-viewer, console, tablet terminal, and the like. The radiographic image reader 18 of the present exemplary embodiment is a personal computer. The radiographic image reader 18 includes, similarly to the console 16 and the radiographic image processing device 14, a CPU, ROM, RAM, a HDD, a display driver, a display 23, an operation input detection section, an operation panel 24, an I/O section, and an I/F section. In order to avoid complexity, only the display 23 and the operation panel 24 thereof are illustrated in FIG. 1, and the other sections are omitted from illustration.

Explanation next follows regarding a schematic configuration of the electronic cassette 20 according to the present exemplary embodiment. In the present exemplary embodiment, explanation follows regarding a case in which the present invention is applied to an indirect conversion type radiation detector 26 in which radiation such as X-rays is first converted into light, and the converted light is then converted into charges. In the present exemplary embodiment, the electronic cassette 20 includes an indirect conversion type radiation detector 26. A scintillator for converting radiation into light is omitted from illustration in FIG. 2.

Plural pixels 100 are arrayed in a matrix formation on the radiation detector 26, with each of the pixels 100 including a sensor portion 103 and a TFT switch 74. The sensor portions 103 receive light, generate charges, and accumulate the generated charges. The TFT switches 74 are switching elements that read the charges accumulated in the sensor portions 103. In the present exemplary embodiment, the sensor portions 103 generate charges upon illumination with light converted by the scintillator.

Figure 2:
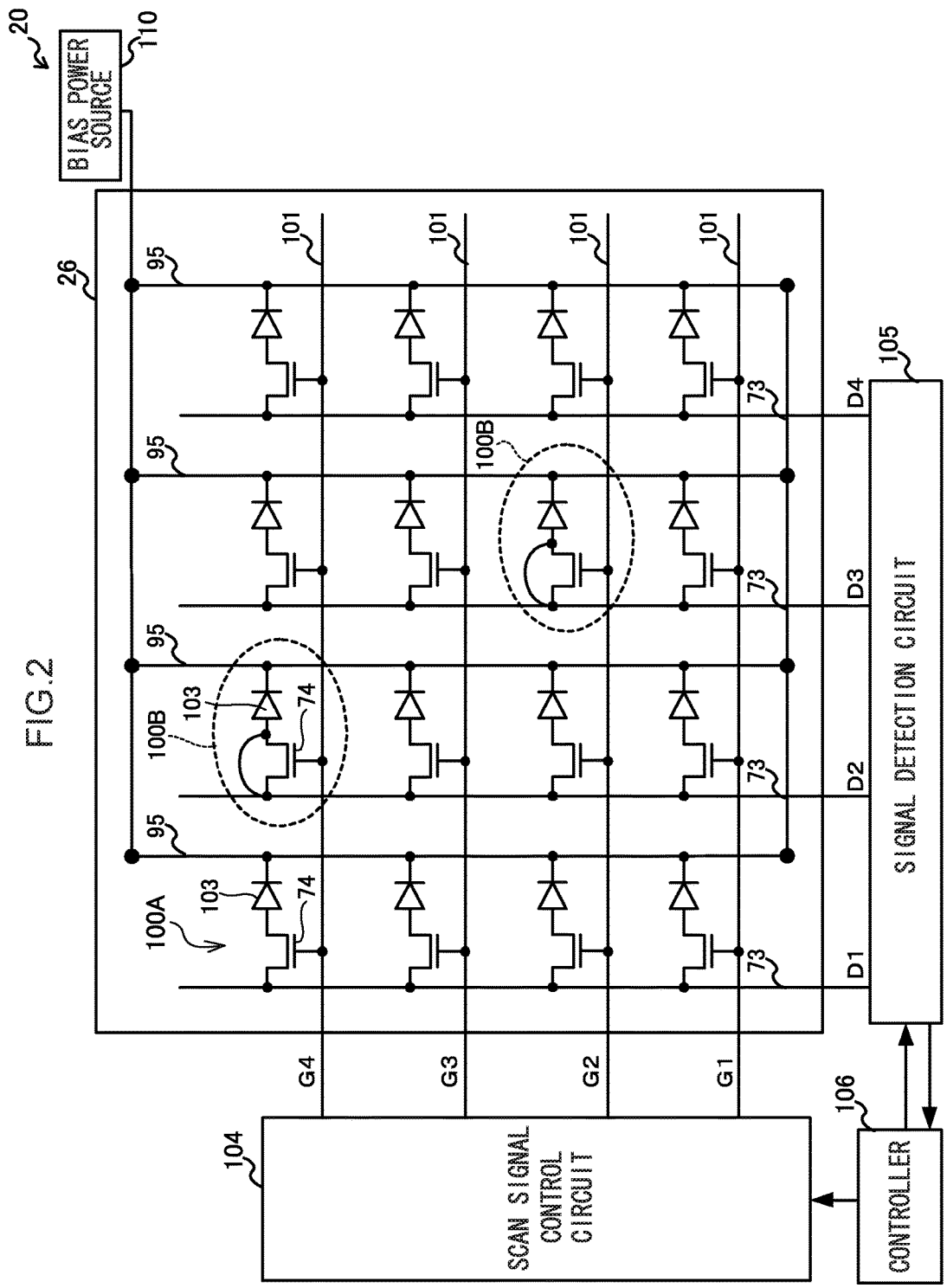
FIG. 2 is a configuration diagram illustrating an example of an overall configuration of an electronic cassette according to the first exemplary embodiment.

Plural of the pixels 100 are arrayed in a matrix formation in a first direction (the gate line direction in FIG. 2) and a direction intersecting with the gate line direction (the signal line direction in FIG. 2). The layout of the pixels 100 is simplified in FIG. 2; however, for example, 1024×1024 of the pixels 100 may be disposed along the gate line direction and the signal line direction.

In the present exemplary embodiment, radiographic imaging pixels 100A and radiation detection pixels 100B are predetermined in the plural pixels 100. The radiation detection pixels 100B are surrounded by intermittent lines in FIG. 2. The radiographic imaging pixels 100A are used to detect radiation and to generate images that represent the radiation. The radiation detection pixels 100B are pixels used for detection of radiation in order to detect the start of radiation irradiation and the like, and are pixels that output charges even during charge accumulation periods (described in detail below).

Plural gate lines 101 that switch the TFT switches 74 ON/OFF, and plural signal lines 73 that read charges accumulated in the sensor portions 103, are provided on the substrate 71 of the radiation detector 26 (see FIG. 4) so as to intersect with each other. In the present exemplary embodiment an individual signal line 73 is provided for each of the pixel rows in the first direction, and an individual gate line 101 is provided for each of the pixel rows in the intersecting direction. There are, for example, 1024 lines respectively provided for the signal lines 73 and for the gate lines 101 in a configuration in which 1024×1024 of the pixels 100 are arrayed in the gate line direction and the signal line direction.

Common electrode lines 95 are provided in the radiation detector 26 parallel to each of the signal lines 73. One end and the other end of each of the common electrode lines 95 are connected together in parallel, and the one ends thereof are connected to a bias power source 110 that supplies a specific bias voltage. The sensor portions 103 are connected to the common electrode lines 95, and are applied with a bias voltage through the common electrode lines 95.

Control signals flow through the gate lines 101 to switch each of the TFT switches 74. Each of the TFT switches 74 is switched by the control signal flowing in the respective gate line 101.

According to the switching state of the TFT switches 74 in the respective pixels 100, electrical signals flow in the respective signal lines 73 according to the charges accumulated in each of the pixels 100. More specifically, switching the TFT switches 74 ON in the respective pixels 100 connected to the respective signal lines 73 causes electrical signals to flow in each of the respective signal lines 73 according to the amount of charge accumulated.

A signal detection circuit 105 is connected to the signal lines 73 to detect the electrical signals flowing in the respective signal lines 73. A scan signal control circuit 104 is also connected to the gate lines 101 to output control signals to each of the gate lines 101 for switching the TFT switches 74 ON/OFF. Illustration in FIG. 2 is simplified to a single signal detection circuit 105 and a single scan signal control circuit 104; however, for example, plural signal detection circuits 105 or scan signal control circuits 104 may be provided, with every specific number of lines (for example 256 lines) of the signal lines 73 or the gate lines 101 connected to each of the signal detection circuits 105 or scan signal control circuits 104, respectively. For example, in cases in which there are 1024 lines respectively provided for the signal lines 73 and the gate lines 101, four of the scan signal control circuits 104 are each connected to 256 of the gate lines 101, and four of the signal detection circuits 105 are each connected to 256 of the signal lines 73.

The signal detection circuit 105 includes an amplification circuit for each of the signal lines 73 to amplify the input electrical signals (see FIG. 6). The electrical signals input by each of the signal lines 73 are amplified by the amplification circuit in the signal detection circuit 105, and converted into digital signals by an analogue-to-digital converter (ADC) (described in detail below).

A controller 106 is connected to the signal detection circuit 105 and the scan signal control circuit 104. The controller 106 performs specific processing, for example noise removal, on the digital signals converted in the signal detection circuit 105, outputs a control signal to the signal detection circuit 105 to indicate timings for signal detection, and outputs a control signal to the scan signal control circuit 104 to indicate timings for outputting scan signals.

The controller 106 of the present exemplary embodiment is configured by a microcomputer. The controller 106 includes a Central Processing Unit (CPU), ROM and RAM, and a non-volatile storage section configured by for example flash memory. The controller 106 performs control to capture radiographic images by using the CPU to execute a program stored in the ROM. The controller 106 also performs processing (interpolation processing) to interpolate image data for each of the radiation detection pixels 100B in image data to which the above specific processing has been performed, so as to generate an image expressing irradiated radiation. Namely, the controller 106 generates an image expressing the irradiated radiation by interpolating image data for each of the radiation detection pixels 100B based on the image data that has been subjected to the above specific processing.

Figure 3:
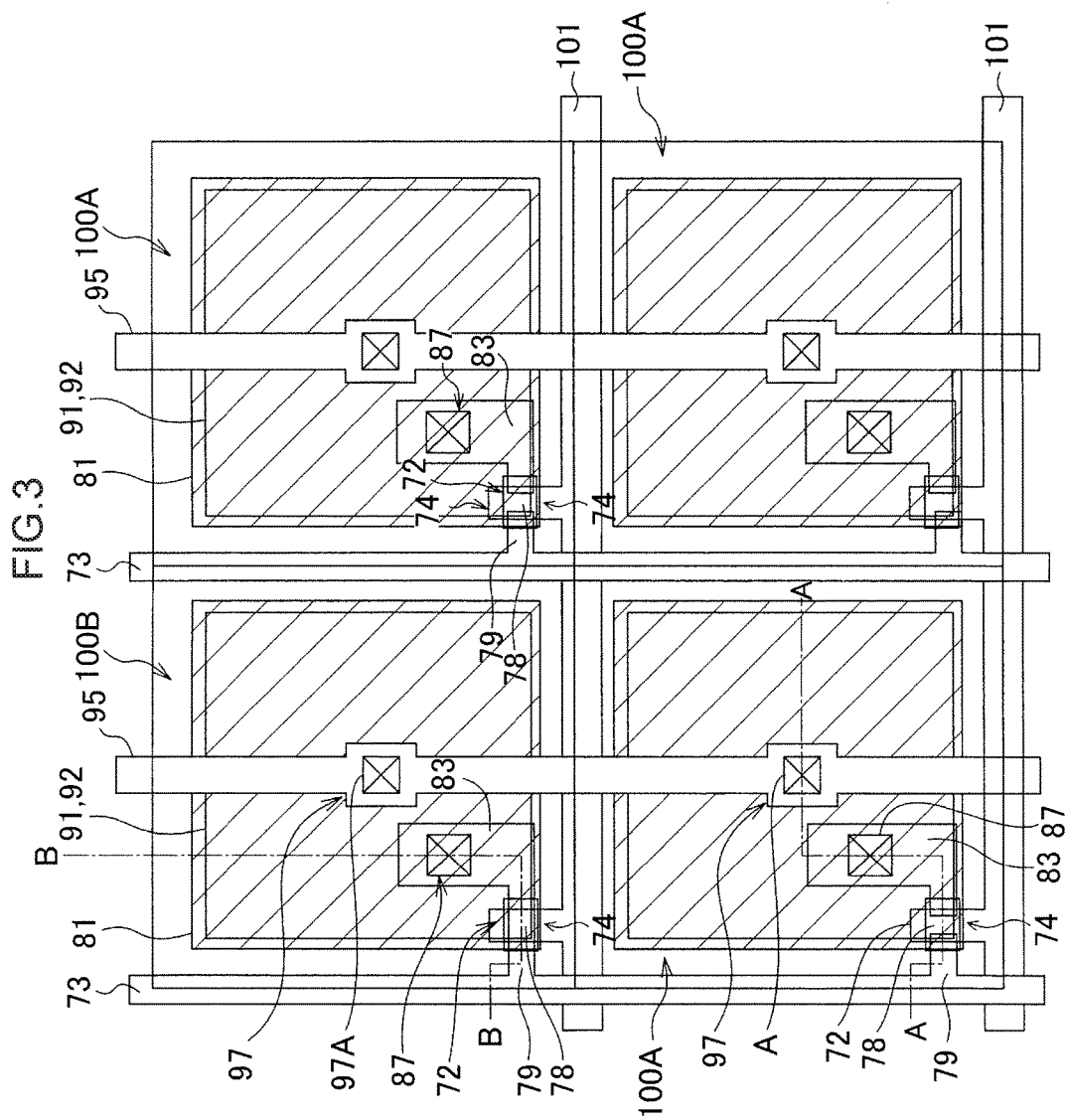
FIG. 3 is a plan view illustrating an example of a configuration of a radiation detector according to the first exemplary embodiment.
Figure 4:
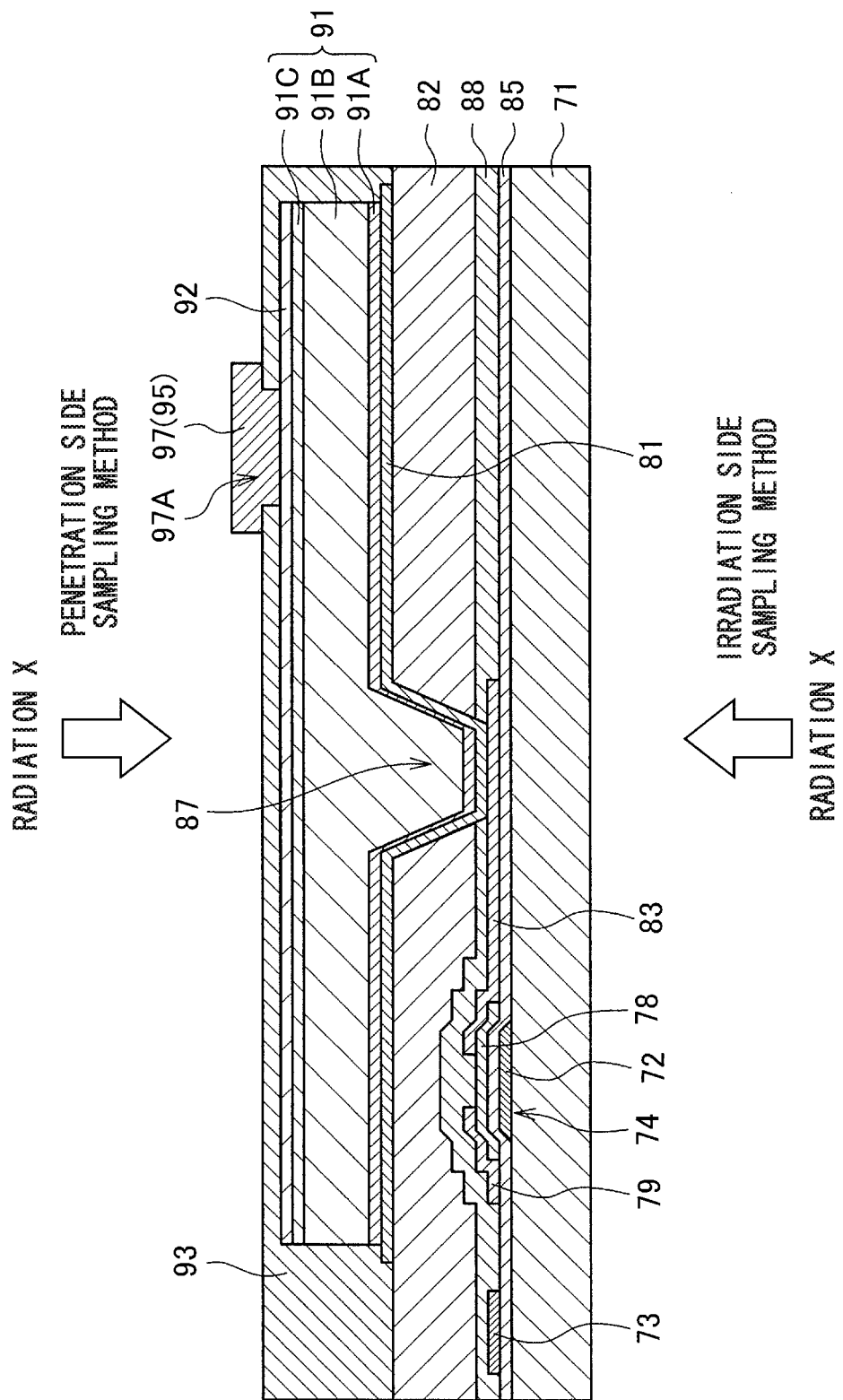
FIG. 4 is a line cross-section of an example of a radiation detector according to the first exemplary embodiment.
Figure 5:
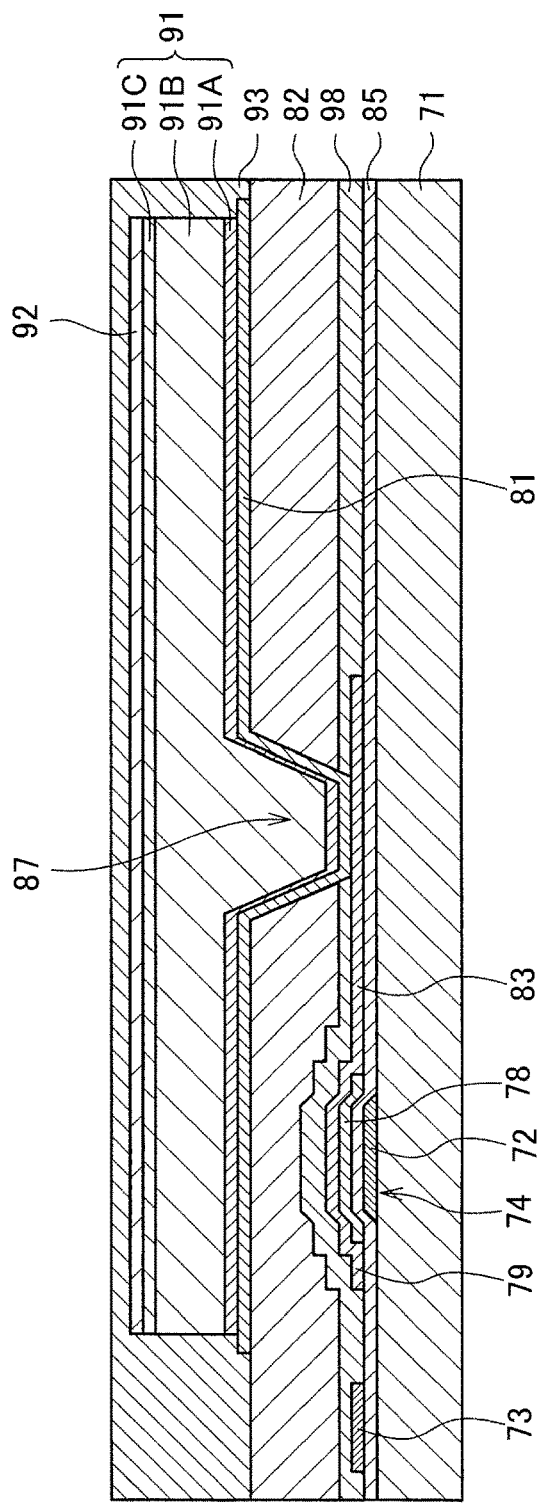
FIG. 5 is a line cross-section of an example of a radiation detector according to the first exemplary embodiment.

FIG. 3 is a plan view illustrating an example of a structure of the indirect conversion type radiation detector 26 according to the present exemplary embodiment. FIG. 4 illustrates a cross-section taken on line A-A of the radiographic imaging pixel 100A of FIG. 3. FIG. 5 is a cross-section taken on line B-B of the radiation detection pixel 100B of FIG. 3.

As illustrated in FIG. 4, the pixels 100A of the radiation detector 26 are configured with the gate line 101 (see FIG. 3) and a gate electrode 72 formed on the insulating substrate 71, such as of non-alkali glass. The gate line 101 and the gate electrode 72 are connected together (see FIG. 3). The wiring layer in which the gate lines 101 and the gate electrodes 72 are formed (this wiring layer is referred to below as the "first signal wiring layer") is formed using Al or Cu, or a stacked layer film of mainly Al or Cu; however, there is no limitation thereto.

An insulation film 85 is formed on one face on the first signal wiring layer, and locations thereof above the gate electrodes 72 act as gate insulation films in the TFT switches 74. The insulation film 85 is, for example, formed from $SiN_x$ using Chemical Vapor Deposition (CVD) film forming.

A semiconductor active layer 78 is formed with an island shape on the insulation film 85 above the gate electrode 72. The semiconductor active layer 78 is a channel portion of the TFT switch 74 and is, for example, formed from an amorphous silicon film.

A source electrode 79 and a drain electrode 83 are formed in a layer above. The wiring layer in which the source electrode 79 and the drain electrode 83 are formed also has the signal line 73 formed therein, as well as the source electrode 79 and the drain electrode 83. The source electrode 79 is connected to the signal line 73 (see FIG. 3). The wiring layer in which the source electrode 79, the drain electrode 83 and the signal line 73 are formed (this wiring layer is referred to below as the "second signal wiring layer") is formed from Al or Cu, or a stacked layer film mainly composed of Al or Cu; however, there is no limitation thereto. An impurity doped semiconductor layer (not illustrated in the drawings) formed for example from impurity doped amorphous silicon is formed between the semiconductor active layer 78 and both the source electrode 79 and the drain electrode 83. Each of the TFT switches 74 used for switching is configured with these elements. The TFT switches 74 may be configured with the source electrode 79 and the drain electrode 83 interchanged according to the polarity of the charge collected and accumulated by lower electrodes 81, described later.

A TFT protection film layer 98 is formed covering the second signal wiring layer over substantially the whole surface (substantially the entire region) of the region where the pixels 100 are provided on the substrate 71, in order to protect the TFT switches 74 and the signal lines 73. The TFT protection film layer 98 is formed, for example, from a material such as $SiN_x$ by, for example, CVD film forming.

A coated intermediate insulation layer 82 is formed on the TFT protection film layer 98. The intermediate insulation layer 82 is formed from a low permittivity (specific permittivity $\varepsilon r=2$ to 4) photosensitive organic material (examples of such materials include positive working photosensitive acrylic resin materials with a base polymer formed by copolymerizing methacrylic acid and glycidyl methacrylate, mixed with a naphthoquinone diazide positive working photosensitive agent) at a film thickness of 1 to 4 μm.

In the radiation detector 26 according to the present exemplary embodiment, inter-metal capacitance between metal disposed in the layers above the intermediate insulation layer 82 and below the intermediate insulation layer 82 is reduced to a small capacitance by the intermediate insulation layer 82. Generally such materials also function as a flattening film, exhibiting an effect of flattening out steps in the lower layers. In the radiation detector 26 according to the present exemplary embodiment, contact holes 87 are formed at positions where the intermediate insulation layer 82 and the TFT protection film layer 98 face towards the drain electrodes 83.

A lower electrode 81 of each of the sensor portions 103 is formed on the intermediate insulation layer 82 so as to cover the pixel region while also filling the contact hole 87. The lower electrode 81 is connected to the drain electrode 83 of the TFT switch 74. In cases in which the thickness of a semiconductor layer 91, described later, is about 1 μm, there are substantially no limitations to the material of the lower electrode 81, as long as it is an electrically conductive material. The lower electrode 81 may therefore be formed using a conductive metal such as an Al material, ITO, or the like.

However, there is insufficient light absorption in the semiconductor layer 91 in a case in which the film thickness of the semiconductor layer 91 is thin (about 0.2 to 0.5 μm). In such cases an alloy or layered film with a main component of a light blocking metal is accordingly preferably used for the lower electrode 81 in order to prevent an increase in leak current occurring due to light illumination onto the TFT switch 74.

The semiconductor layer 91 is formed on the lower electrode 81 and functions as a photodiode. In the present exemplary embodiment, a photodiode of PIN structure stacked with an n+ layer, an i layer and a p+ layer (n+ amorphous silicon, amorphous silicon, p+ amorphous silicon) is employed as the semiconductor layer 91, with an n+ layer 91A, an i layer 91B and a p+ layer 91C stacked in this sequence from the bottom layer. The i layer 91B generates charges (pairs of free electrons and free holes) on illumination with light. The n+ layer 91A and the p+ layer 91C function as contact layers and electrically connect the i layer 91B to the lower electrodes 81 and upper electrodes 92, described later.

The upper electrode 92 is respectively formed separately on the semiconductor layers 91. A material with high light-transparency such as ITO or Indium Zinc Oxide (IZO) is for example used for the upper electrode 92. In the radiation detector 26 of the present exemplary embodiment, the sensor portions 103 are each configured including the upper electrode 92, the semiconductor layer 91 and the lower electrode 81.

A coated intermediate insulation layer 93 is formed over the intermediate insulation layer 82, the semiconductor layer 91 and the upper electrode 92, and is formed so as to cover the semiconductor layers 91, with openings 97A formed in portions corresponding to above the upper electrode 92.

The common electrode lines 95 are formed on the intermediate insulation layer 93 from Al or Cu, or from stacked layer films of an alloy of mainly Al or Cu. The common electrode lines 95 are formed in the vicinity of the openings 97A with a contact pad 97, and are electrically connected to the upper electrodes 92 through the openings 97A of the intermediate insulation layer 93.

On the other hand, as illustrated in FIG. 5, in the radiation detection pixels 100B of the radiation detector 26, the TFT switches 74 are formed such that the source electrode 79 and the drain electrode 83 are in contact with each other. Namely, in the pixels 100B, the sources and drains of the TFT switches 74 are shorted. Thus, in the pixels 100B, charges collected by the lower electrodes 81 flow out to the signal lines 73 irrespective of the switching state of the TFT switches 74.

In the radiation detector 26 formed in this manner, a further protection layer is formed from an insulating material with low light absorptivity as required, and then the scintillator that serves as a radiation conversion layer is stuck to the surface thereof using a bonding resin with low light absorptivity. Moreover, the scintillator may be formed using a vacuum deposition method. As a scintillator, preferably a scintillator is employed that generates fluorescence having a comparatively wide wavelength region, so as to enable light to be emitted in a wavelength region capable of being absorbed. Examples of materials for such scintillators include CsI: Na, CaWO$_4$, YTaO$_4$: Nb, BaFX: Eu (wherein X is Br or Cl), or LaOBr: Tm, and GOS. Specifically, in cases in which imaging is performed using X-rays as the radiation X, preferably cesium iodide (CsI) is included, and CsI: Tl (thallium doped cesium iodide) or CsI: Na, that have emission spectra of 400 nm to 700 nm when irradiated with X-rays, are particularly preferably used. The emission peak wavelength in the visible light region of CsI: Tl is 565 nm. In cases in which a scintillator containing CsI is used as the scintillator, preferably a rectangles shaped columnar crystal structure is formed using a vacuum deposition method.

As illustrated in FIG. 4, in cases in which the radiation detector 26 is irradiated with radiation X from the side where the semiconductor layer 91 is formed, and radiographic images are read by the TFT substrate provided on the back side with respect to the radiation X incident face, i.e., in Penetration Side Sampling (PSS) method, light is emitted with higher intensity at the upper face in FIG. 4 of the scintillator provided on the semiconductor layer 91. However, in cases in which radiation X is irradiated from the TFT substrate side and radiographic images are read by the TFT substrate provided on the front side with respect to the radiation X incident face, i.e., in an Irradiation Side Sampling (ISS) method, radiation X that has passed through the TFT substrate is incident to the scintillator and light is emitted with higher intensity from the TFT substrate side of the scintillator. Each of the sensor portions 103 of each of the pixels 100 provided in the TFT substrate generates charges due to the light generated by the scintillator. The radiation detector 26 therefore gives a higher resolution of captured radiographic images in cases in which an ISS method is employed than in cases in which a PSS method is employed, since the [intense] light emission position of the scintillator is closer to the TFT substrate.

Note that the radiation detector 26 is not limited to that illustrated in FIG. 3 to FIG. 5, and various modifications are possible. For example, in cases in which a PSS method is employed, since there is only a low possibility of radiation X arriving, a combination of another image pickup device such as a Complementary Metal-Oxide Semiconductor (CMOS) image sensor that has a low durability to radiation X and TFTs may be used instead of the above configuration. Alternatively, configuration may be made by substituting with a Charge Coupled Device (CCD) image sensor that transmits charge while shifting by a shift pulse that is equivalent to the gate signal for TFTs.

Moreover, for example, a flexible substrate may be used in the radiation detector 26. An ultra-thin glass substrate produced by recently developed float technology is preferably applied as a substrate for such a flexible substrate in order to improve the transmissivity to radiation. Examples of ultra-thin glass that may be applied in such cases include, for example, that described in "Asahi Glass Company (AGC) Develops World's Thinnest Sheet Float Glass at Just 0.1 MM", Internet <URL: http://www.agc.com/news/2011/0516.pdf> (retrieved Aug. 20, 2011).

Explanation next follows regarding a schematic configuration of a signal detection circuit 105 of the present exemplary embodiment. FIG. 6 is a schematic configuration diagram illustrating an example of the signal detection circuit 105 of the present exemplary embodiment. The signal detection circuit 105 of the present exemplary embodiment includes amplification circuits 120 and an analogue-to-digital (ADC) converter 124. Although omitted from illustration in FIG. 6, the amplification circuits 120 are provided for each signal line 73. Namely, the signal detection circuit 105 includes the same number of plural amplification circuits 120 as the number of signal lines 73 of the radiation detector 26.

The amplification circuit 120 is configured as a charge amplification circuit and is configured including an amplifier 121 such as an operational amplifier, a capacitor C connected in parallel to the amplifier 121, and a switch SW1 that is connected in parallel to the amplifier 121 and is used for charge resetting.

In the amplification circuits 120, charges (electrical signals) are read by the TFT switches 74 of the pixels 100 with the charge reset switch SW1 in the OFF state. The charges read by the TFT switches 74 are accumulated in the capacitors C, such that the voltage value output from the amplifier 121 is increased according to the accumulated charge amount.

Moreover, the controller 106 applies a charge reset signal to the charge reset switch SW1 to control to ON/OFF switch the charge reset switch SW1. Note that when the charge reset switch SW1 is in the ON state, the input side and the output side of the amplifier 121 are shorted, and so charge of the capacitors C is discharged.

The ADC 124 has a function to convert an electrical signal that is an analogue signal input from the amplification circuits 120 in an ON state of a sample and hold (S/H) switch SW into a digital signal. The ADC 124 sequentially outputs to the controller 106 electrical signals that have been converted into digital signals. Note that the ADC 124 in the present exemplary embodiment is input with the electrical signals output from all of the amplification circuits 120 provided in the signal detection circuit 105. Namely, the signal detection circuit 105 of the present exemplary embodiment is provided with a single ADC 124 irrespective of the number of the amplification circuits 120 (the signal lines 73).

In the present exemplary embodiment, the electrical signals (charge data) of the signal lines 73 that are connected to the radiation detection pixels 100B (at least one of D2 or D3 in FIG. 2, say D2) are detected by the amplification circuits 120 of the signal detection circuit 105. The control section 106 compares the value of the digital signal converted by the signal detection circuit 105 against a predetermined detection threshold value, and detects whether or not radiation has been irradiated depending on whether or not the digital signal value is the threshold value or greater. In the present exemplary embodiment, detection relating to radiation irradiation is performed without a need of a control signal from outside (for example, from the radiographic image processing device 14). Detection by the controller 106 as to whether or not radiation has been irradiated is not limited to comparison against a detection threshold value. For example, detection may be based on preset conditions, such as, for example, a number of detection times or the like.

Note that "detection" of an electrical signal in the present exemplary embodiment refers to electrical signal sampling.

Explanation next follows regarding a flow of operation during radiographic imaging by the electronic cassette 20 configured as described above, focusing on an operation for detecting the occurrence of noise caused by external disturbance. Explanation first follows regarding noise caused by external disturbance. Noise (charge) may be generated in the sensor portions 103 due to external disturbance such as impacts or electromagnetic waves, and in particular vibrations or the like. Electrical signals (charge data) according to the noise (charges) occurring due to external disturbance have different characteristics to the electrical signals (charge data) according to charges generated by radiation irradiation during normal radiographic imaging, in particular exhibiting different change with time. For example, when there is noise, the polarity of the electrical signal may be the opposite to normal due to charges flowing in the opposite direction. In cases in which there is noise, there is amplitude in the waveform representing the change of the electrical signals (charge data) with time.

Figure 7A:
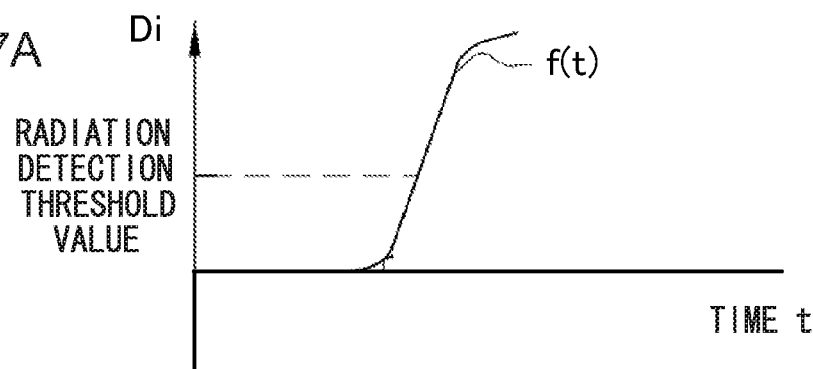
FIG. 7A is a graph illustrating change with time of an electrical signal in a case in which radiation is irradiated onto a radiation detector according to the first exemplary embodiment, showing change with time of an electrical signal Di.
Figure 7B:
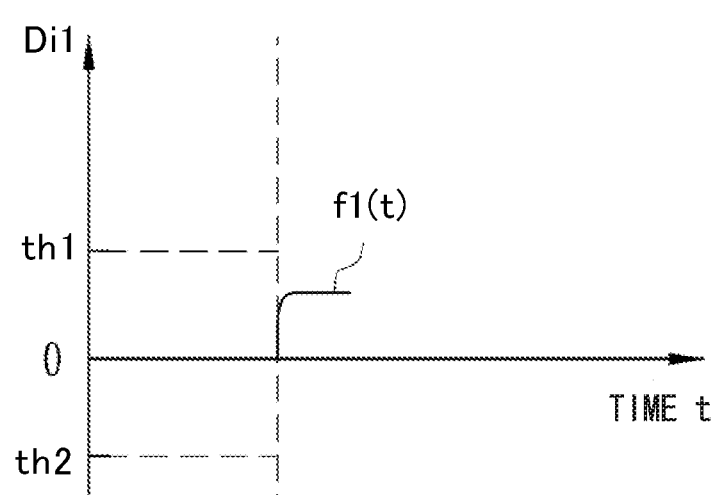
FIG. 7B is a graph illustrating change with time of an electrical signal in a case in which radiation is irradiated onto a radiation detector according to the first exemplary embodiment, showing change with time of a first derivative value Di1.
Figure 7C:
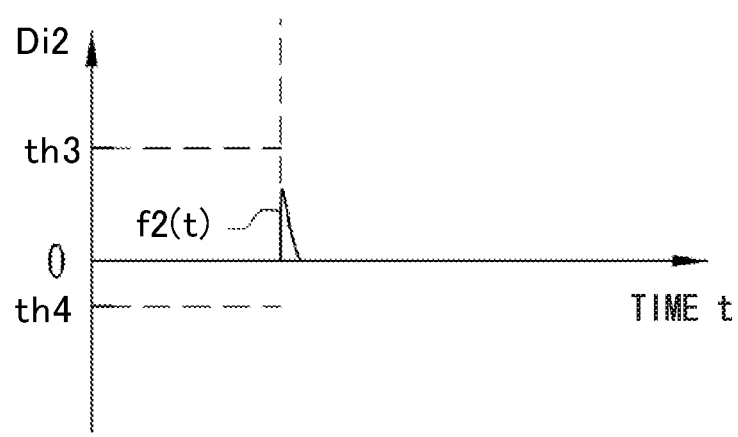
FIG. 7C is a graph illustrating change with time of an electrical signal in a case in which radiation is irradiated onto a radiation detector according to the first exemplary embodiment, showing change with time of a second derivative value Di2.
Figure 8A:
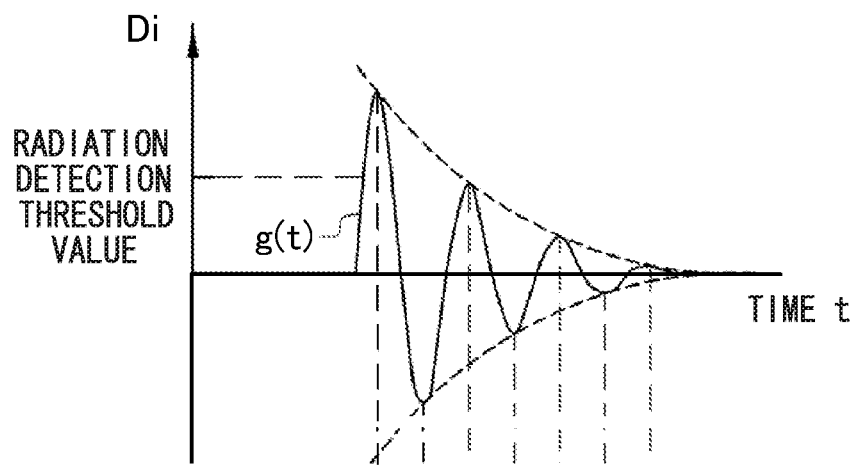
FIG. 8A is a graph illustrating change with time of an electrical signal in a case in which noise has occurred in a radiation detector according to the first exemplary embodiment, showing change with time of an electrical signal Di.
Figure 8B:
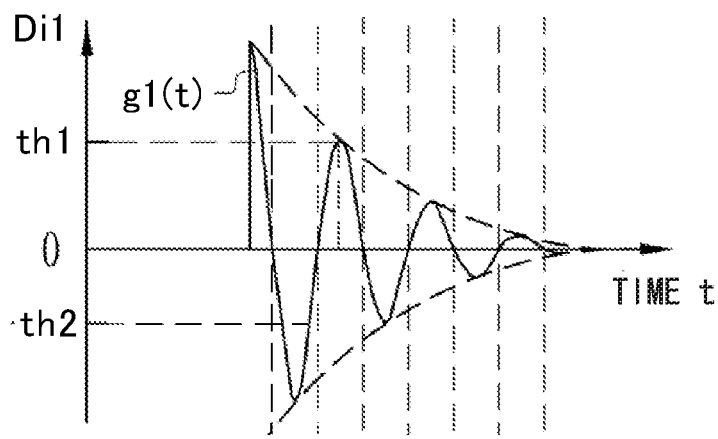
FIG. 8B is a graph illustrating change with time of an electrical signal in a case in which noise has occurred in a radiation detector according to the first exemplary embodiment, showing change with time of a first derivative value Di1.
Figure 8C:
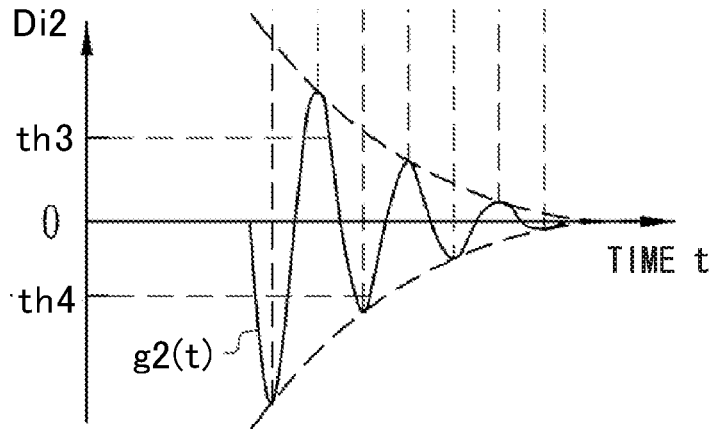
FIG. 8C is a graph illustrating change with time of an electrical signal in a case in which noise has occurred in a radiation detector according to the first exemplary embodiment, showing change with time of a second derivative value Di2.

Detailed explanation follows regarding differences between the electrical signals due to radiation irradiation, and the electrical signals due to noise in the radiation detector 26. FIG. 7A to FIG. 7C are graphs illustrating change with time in electrical signals in cases in which radiation is irradiated onto the radiation detector 26 according to the present exemplary embodiment. FIG. 7A, FIG. 7B, and FIG. 7C respectively illustrate change with time in an electrical signal Di, a first derivative value Di1 of the electrical signal Di, and a second derivative value Di2 of the electrical signal Di. FIG. 8A to FIG. 8C are graphs illustrating change with time in electrical signals in cases in which noise has occurred in the radiation detector 26 according to the present exemplary embodiment. FIG. 8A, FIG. 8B, and FIG. 8C respectively illustrate change with time in the electrical signal Di, the first derivative value Di1 of the electrical signal Di, and the second derivative value Di2 of the electrical signal Di.

As illustrated in FIG. 7A, on radiation irradiation, the electrical signal Di increases, and changes with time as expressed by function $f(t)$ at time t. In the radiation detector 26 of the present exemplary embodiment, radiation irradiation start is detected by whether or not the electrical signal Di exceeds a detection threshold value. Similarly to the electrical signal Di in cases in which radiation is irradiated, the electrical signal Di generated by noise in FIG. 8A changes with time, as expressed by function $g(t)$ at time t. However, in this case the waveform is a sine wave with a fixed cycle and gradually decreasing amplitude, namely the waveform of an attenuating oscillation. The first derivative obtained therefrom is, as illustrated in FIG. 8B, a waveform $g1(t)$ with a phase difference of 90° therefrom.

As illustrated in FIG. 7B, the first derivative $f1(t)$ of the function $f(t)$ when radiation is irradiated has a sharp rise due to radiation irradiation, then quickly becomes constant. In contrast thereto, the first derivative $g1(t)$ of the function $g(t)$ of the waveform due to noise of FIG. 8B merely differs in phase, with no change in the waveform of the attenuating signal. In cases in which radiation has truly been irradiated, the first derivative $f1(t)$ has constantly positive polarity; however, in the case of noise, the polarity reverses in the first derivative $g1(t)$ and swings back and forth with amplitude between positive polarity and negative polarity.

As illustrated in FIG. 7C, in cases in which radiation is irradiated, the second derivative $f2(t)$ of the waveform function $f(t)$ behaves as what is referred to as a Gaussian function. In contrast thereto, the second derivative $g2(t)$ of the waveform function $g(t)$ due to noise of FIG. 8C is similar to the first derivative, merely differing in phase, with no change to the waveform of the attenuating signal. Thus, similarly to for the first derivative, for the second derivative also the second derivative f2 (t) when radiation is truly irradiated has a polarity that is constantly a positive polarity; however, in the case of noise, the polarity reverses in the second derivative g2 (t), exhibiting negative polarity, and swings back and forth with amplitude between positive polarity and negative polarity.

As can be seen by comparing FIG. 7A to FIG. 7C with FIG. 8A to FIG. 8C, in cases in which radiation has truly been irradiated, the first derivative f1 (t) is smaller than the first derivative g1 (t) for noise. Similarly, in cases in which radiation has truly been irradiated, the second derivative f2 (t) is smaller than the second derivative g2 (t) for noise. Therefore, by predetermining noise determination threshold values (th1, th2) to distinguish between the first derivative f1 (t) and the first derivative g1 (t), determination may be made that noise has occurred in cases in which the change with time of the electrical signal has exceeded the respective noise determination threshold value. Similarly, by predetermining noise determination threshold values (th3, th4) to distinguish between the second derivative f2 (t) and the second derivative g2 (t), determination may be made that noise has occurred in cases in which the change with time of the electrical signal has exceeded the respective noise determination threshold value.

In the present exemplary embodiment, detection for the electrical signal (charge data) output from the radiation detection pixels 100B continues even after radiation irradiation start has been detected, and the controller 106 determines whether or not noise has occurred by whether or not the change with time in the electrical signal (charge data) within a specific detection period has the characteristics of noise described above. More specifically, as stated above, determination may be made as to whether or not the polarity of the electrical signal reverses from normal, or determination may be made as to whether or not the slope is decreasing by taking a derivative (for example the first derivative or the second derivative) of the electrical signal (charge data) output within a specific period, and making determination that noise has not occurred in cases in which the slope can be approximated to being substantially constant or gradually rising. Or, for example, determination may be made by using a noise determination threshold value. Preferably a combination of plural types of determination is made in order to raise the detection precision of noise occurrence.

The specific period referred to above differs depending on the imaging conditions and the electronic cassette 20, and may, for example, be obtained by experimentation in advance or the like as a percentage of the accumulation period during which charges are accumulated in the pixels 100 on irradiation of radiation.

In cases in which a strong impact is received as an external disturbance, charges may be generated in specific signal lines 73 or the like and the generated noise may differ depending on the signal line 73. Or, the generated noise may also differ according to the region where the pixels 100 are provided. In such cases, the noise occurring in each of the signal lines 73 may be obtained in advance, such as by experimentation, and different determination criteria may be adopted according to each signal line 73. Further, the region where the pixels 100 are provided (the radiation irradiation region) may be divided into plural regions, the occurrence of noise may be obtained in advance, such as by experimentation, for each of the divided regions, and different determination criteria may be adopted for each region. For example, the above false detection determination threshold values (th1 to th4) may be predetermined according to each signal line 73 and according to each region. In cases in which the determination criteria differ according to the signal line 73 and the region in this manner, the occurrence of noise is determined for each of the signal lines 73 and for each of the regions. A decision that noise has occurred is made in cases in which one or more, or a specific number or more, of the determination results is that noise has occurred, and the current operation of the electronic cassette 20 is stopped. For example, the accumulation period may be ceased.

Detailed explanation next follows regarding a flow of operation during radiographic imaging by the electronic cassette 20 of the present exemplary embodiment. FIG. 9 is a flowchart illustrating an example of a flow of operation during radiographic imaging.

The electronic cassette 20 of the present exemplary embodiment captures a radiographic image by detecting radiation irradiation start, accumulating charges in each of the pixels 100 of the radiation detector 26, and outputting a radiographic image based on image data according to the accumulated charges.

In the present exemplary embodiment, when performing radiographic imaging, transition to an imaging mode is notified to the electronic cassette 20. At step S100, transition is made to the imaging mode according to such notification.

At the next step S102, after notification of transition to the imaging mode, transition is then made to a radiation detection standby state in which detection is made for radiation. At step S104, determination is made as to whether or not radiation irradiation start has been detected. In cases in which there has been no detection, negative determination is made, and processing returns to step S102 and the present processing is repeated.

When radiation has been irradiated from the radiation generation device 12, the irradiated radiation is absorbed by the scintillator and converted into visible light. The radiation may be irradiated onto either the front side or the back side of the radiation detector 26. The light converted into visible light by the scintillator is irradiated onto the sensor portion 103 of each of the pixels 100.

Charges are generated in the sensor portions 103 upon irradiation with the light. The generated charges are collected in the lower electrodes 81.

In the radiographic imaging pixels 100A, the charges collected in the lower electrodes 81 are accumulated since the drain electrode 83 and the source electrode 79 are not shorted. However, in the radiation detection pixels 100B, the charges collected in the lower electrodes 81 flow out into the signal lines 73 since the drain electrode 83 and the source electrode 79 are shorted.

In the electronic cassette 20 of the present exemplary embodiment, as described above, the electrical signals (charge data) output from the radiation detection pixels 100B are detected in the amplification circuits 120 of the signal detection circuit 105, the controller 106 compares the detected electrical signals (charge data) against predetermined threshold values for detection, and detection of radiation irradiation start is made by whether or not the detected electrical signals have reached the threshold value or greater. In a case in which irradiation start has been detected, affirmative determination is made, processing proceeds to step S106, and transition is made to a charge accumulation state in which charges are accumulated in the radiation detector 26. Consequently, at the next step S108, accumulation of charges generated according to radiation irradiated onto each of the pixels 100 is initiated.

The radiographic imaging pixels 100A of the radiation detector 26 adopt a charge accumulated state since the TFT switches 74 are still in the OFF state. However, the radiation detection pixels 100B output charges to the signal detection circuit 105 even during the charge accumulation period (the OFF state of the TFT switches 74) since the TFT switches 74 are shorted. The S/H switch SW is switched ON/OFF at specific timings irrespective of charge accumulation periods and reading periods. Therefore, data of the charges output from the radiation detection pixels 100B are input to the controller 106 as electrical signals (charge data), through the amplification circuits 120 and the ADC 124 of the signal detection circuit 105.

At the next step S110, determination is made as to whether or not noise has occurred. Whether or not noise has occurred is determined by continuously detecting the electrical signals (charge data) output from the radiation detection pixels 100B, as described above, and determining whether or not the change with time of the electrical signals (charge data) within the specific detection period has the characteristics of noise, as described above.

In a case in which noise is determined to have occurred, affirmative determination is made, and processing proceeds to step S112, driving of the electronic cassette 20 is controlled, and the accumulation period is ceased. Charge accumulation is interrupted, and transition is made again to a radiation detection period. In the present exemplary embodiment, notification is made to the user, such as a doctor, that noise has occurred. The notification method is not particularly limited and may, for example, be display on the display 50 of the console 16 through the radiographic image processing device 14. Notification may also be made, for example, by audio or the like.

In cases in which noise has occurred, as well as interrupting charge accumulation, the radiation generator 12 is preferably controlled by the radiation controller 62 to interrupt radiation irradiation. Interrupting the radiation irradiation in this manner enables unnecessary exposure of the subject 30 to be reduced, and enables preparation for re-imaging to be performed.

Transition may be made to the radiation detection period immediately after ending the accumulation period; however, in order to eliminate mistaken determination of radiation irradiation start detection due to the charges accumulated during the accumulation period, a reset operation may be performed prior to transitioning to the radiation detection period to reset the charges accumulated in the pixels 100 by reading and discarding the electrical signals (charge data). Therefore, in the present exemplary embodiment, processing returns to step S102 after performing a reset operation at step S114, and the present processing is repeated. During performance of the reset operation, since the reset operation period is a period not sensitive to radiation (non-detection period), preferably a simultaneous reset operation is performed for the plural gate lines 101 in order to shorten this period. Further, during the reset operation, control may be made by the radiation controller 62 to the radiation generator 12 to prevent radiation irradiation.

In a case in which the occurrence of noise has not been detected, processing proceeds to step S118 and determination is made as to whether or not a specific time has elapsed from the detection of radiation irradiation start based on a timer, not illustrated in the drawings. Negative determination is made in a case in which a specific time has not yet elapsed, and processing returns to step S110 and the present processing is repeated. In the present exemplary embodiment, detection for the occurrence of noise is made continuously during the accumulation period.

In a case in which a specific time has elapsed, processing proceeds to step S120 and transition is made to a charge reading state to read the accumulated charges. During the reading period, specifically, the TFT switches 74 of the pixels 100A are switched ON in sequence by applying an ON signal through the gate lines 101 in sequence to the gate electrodes 72 of the TFT switches 74, and the charges are read by outputting electrical signals according to the charge amounts accumulated in the respective pixels 100A into the signal lines 73.

After charge reading has ended, processing proceeds to step S122 and determination is made as to whether or not to end radiographic imaging. In cases in which successive radiographic imaging is to be performed, such as in video imaging, negative determination is made and processing returns to step S102, transition is made once more to a standby state, and the present processing is repeated. In a case in which imaging is to be ended, affirmative determination is made and the present processing is ended.

Thus, as explained above, in the electronic cassette 20 of the present exemplary embodiment, upon irradiation of radiation, over the specific detection period, the signal detection circuit 105 detects the electrical signals (charge data) of charges generated according to the radiation output over the charge accumulation period from the radiation detection pixels 100B. Moreover, the controller 106 determines whether or not the change with time of the electrical signals (charge data) has the predetermined characteristics of noise. Determination is made that noise has occurred in a case in which such characteristics are present, operation of the electronic cassette 20 is stopped, the charge accumulation period is interrupted (ceased), and transition is made to a radiation detection period.

The present exemplary embodiment is accordingly capable of detecting whether or not noise caused by external disturbance has occurred based on the electrical signals (charge data) output from the radiation detection pixels 100B during the charge accumulation period. Driving of the electronic cassette 20 is stopped immediately in the case in which occurrence of noise has been detected. Thus, it is possible to detect noise and control the imaging operation of the electronic cassette 20 without any delay in cases in which noise caused by external disturbance has occurred, whereby the time from noise occurrence detection to re-imaging can be shortened. This thereby enables unnecessary exposure of the subject 30 (ineffective exposure that does not contribute to generation of a radiographic image) to be reduced.

In the present exemplary embodiment, a configuration to detect radiation irradiation start in the electronic cassette 20 is used to detect noise occurrence. This thereby enables configuration to detect noise occurrence to be simplified.

Figure 10:
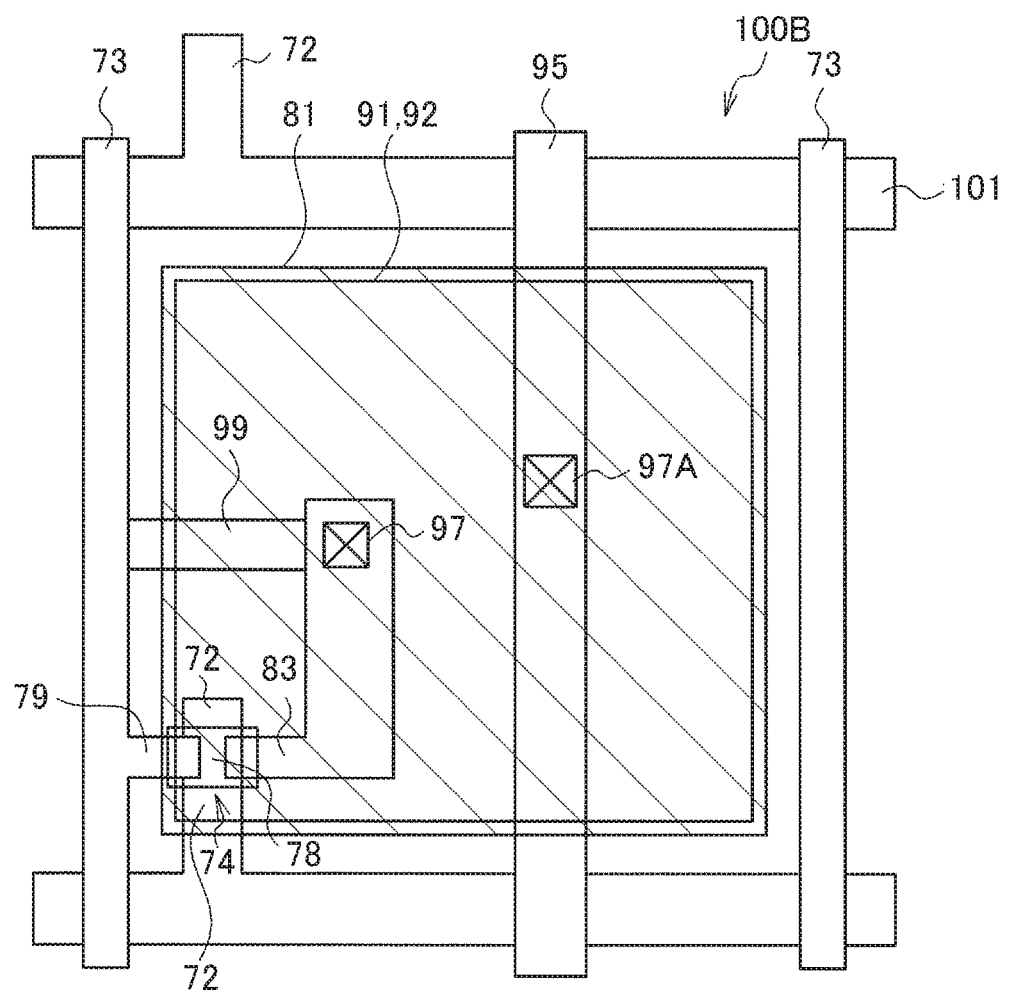
FIG. 10 is a plan view illustrating an example of a configuration of a radiation detection pixel according to another embodiment.
Figure 11:
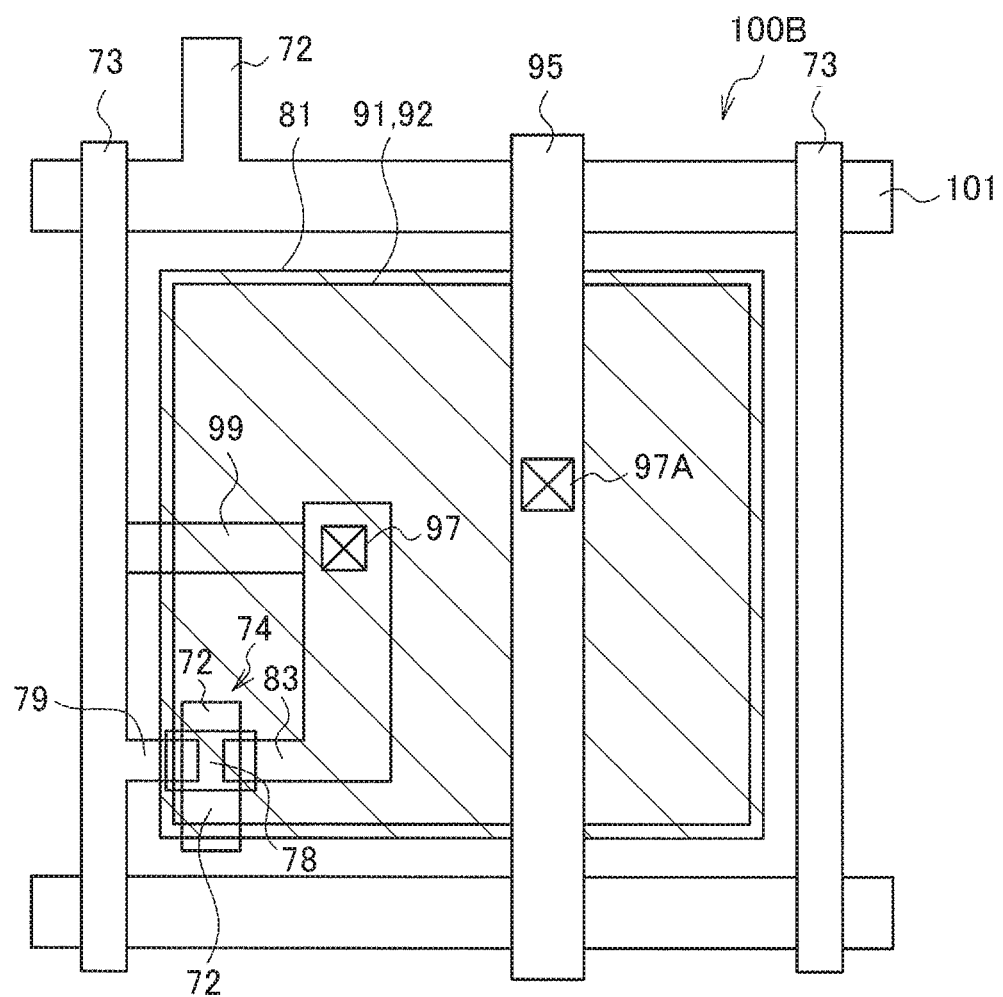
FIG. 11 is a plan view illustrating an example of a configuration of a radiation detection pixel according to another embodiment.

Explanation has been given above in which pixels equipped with TFT switches 74 with shorted sources and drains are used as the radiation detection pixels 100B; however, there is no limitation thereto. For example, as illustrated in FIG. 10, a connection line 99 may be formed from partway along the drain electrode 83 to connect to the signal line 73. In such cases too, the sources and drains of the TFT switches 74 are effectively shorted. In the above exemplary embodiment and as illustrated in FIG. 10, in cases in which the sources and drains of the TFT switches 74 are shorted, the gate electrode 72 may be formed separated from the respective gate lines 101, as illustrated in FIG. 11.

Figure 12:
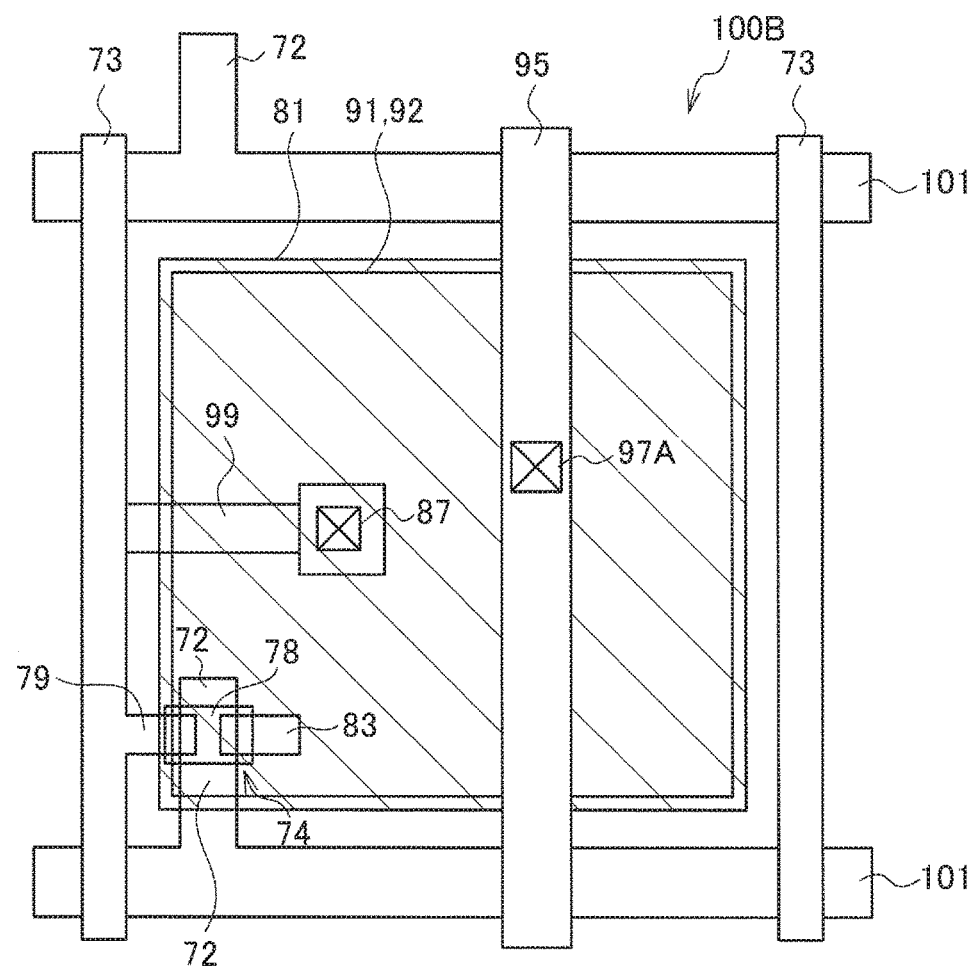
FIG. 12 is a plan view illustrating an example of a configuration of a radiation detection pixel according to another embodiment.

Moreover, for example, as illustrated in FIG. 12, configuration may be made such that the drain electrode 83 and the contact hole 87 in the radiation detection pixels 100B are not connected together electrically by forming the connection line 99, and connecting the sensor portions 103 and the signal lines 73 through the connection line 99 and the contact hole 87.

Moreover, although explanation has been given above of a case in which pixels with shorted TFT switches 74 are used as the radiation detection pixels 100B, pixels that do not have shorted TFT switches 74 may be used as the radiation detection pixels 100B. In such cases, control of the TFT switches 74 of the radiation detection pixels 100B is performed independently of control of the TFT switches 74 of the pixels 100A. Moreover, the pixels 100B in such cases may be specific pixels 100 of the radiation detector 26, or may be provided as different pixels to the pixels 100 in the radiation detector 26.

Moreover, in the radiation detector 26 of the electronic cassette 20 of the present exemplary embodiment (see FIG. 2), the radiation detection pixels 100B are connected to some of the signal lines 73; however, there is no limitation thereto. For example, the radiation detection pixels 100B may be provided at positions connected to all of the signal lines 73, and there is no particular limitation to the positions where the radiation detection pixels 100B are provided.

Second Exemplary Embodiment

In the first exemplary embodiment described above, the occurrence of noise caused by external disturbance is detected together with detection of radiation irradiation start based on electrical signals according to charges generated by the radiation detection pixels 100. In contrast, in the present exemplary embodiment, explanation is given regarding a case in which the occurrence of noise caused by external disturbance is detected together with detection of radiation irradiation start based on, for example, charges flowing in the common electrode lines.

Note that since the present exemplary embodiment includes configuration and operation substantially the same as that of the first exemplary embodiment, configuration and operation that is substantially the same is indicated as such, and detailed explanation thereof is omitted. The overall outline configuration of a radiographic imaging system 10 of the present exemplary embodiment is substantially the same as that of the first exemplary embodiment, and so detailed explanation thereof is omitted.

Explanation follows regarding an outline configuration of an electronic cassette 20 according to the present exemplary embodiment. Similarly to the first exemplary embodiment, in the present exemplary embodiment explanation is given regarding a case in which the present invention is applied to the indirect conversion type radiation detector 26. FIG. 13 is a configuration drawing illustrating an example of an overall configuration of the electronic cassette 20 according to the present exemplary embodiment. The electronic cassette 20 of the present exemplary embodiment is not provided with the radiation detection pixels 100B that are provided in the first exemplary embodiment, and all of the pixels have a similar configuration.

In the electronic cassette 20 of the present exemplary embodiment, the common electrode lines 95 are connected to the bias power source 110 through a current detector 122. In cases in which a bias voltage is applied to each of the pixels 100 in the present exemplary embodiment, the bias voltage is applied to each of the pixels 100 directly, not through the current detector 122.

The current detector 122 has a function to detect current flowing through the common electrode lines 95 from the respective pixels 100. The controller 106 detects radiation irradiation start by comparing a current value of the current flowing in the common electrode lines 95 detected by the current detector 122 against a predetermined detection threshold value, and determining whether or not the current value is the threshold value or greater. Current flows in the common electrode lines 95 according to the charges (charge amounts) generated in the sensor portions 103 of the pixels 100 when the radiation detector 26 is irradiated with radiation. Accordingly, in the present exemplary embodiment, a relationship between current values of the current flowing in the common electrode lines 95 and the amount of radiation with which the radiation detector 26 is irradiated is obtained in advance, and a current value for detecting irradiation start is set in advance as the threshold value. Note that since an increase in the charges (charge amounts) generated by the sensor portions 103 is accompanied by an increase in the current value of the current flowing in the common electrode lines 95, the current value of the current flowing in the common electrode lines 95 increases accompanying increase in the amount of irradiated radiation.

Accordingly, an increase in the charges (charge amounts) generated by the sensor portions 103 is accompanied by an increase in the current value of the current flowing in the common electrode lines 95. As explained in the first exemplary embodiment, in a case in which noise caused by external disturbance occurs, generating charges in the pixels 100, then the current value of the current flowing in the common electrode lines 95 changes accordingly therewith. Therefore, in the present exemplary embodiment, the controller 106 detects the occurrence of noise according to, for example, whether or not a change with time such as that described above occurs in the current flowing in the common electrode lines 95, or whether or not the noise determination threshold value has been exceeded. Obviously in such cases, the change with time of the current value of the current flowing in the common electrode lines 95, and the noise determination threshold value, may be obtained in advance through experimentation or the like.

In the electronic cassette 20 of the present exemplary embodiment, the flow of operation during radiographic imaging is substantially the same as that in the first exemplary embodiment, and so detailed explanation is given regarding only differing operation, using the flowchart used in the first exemplary embodiment (FIG. 9).

At step S100, transition is made to the imaging mode, and at step S102 the cassette stands by for detection of radiation irradiation start (enters the radiation detection period). In the present exemplary embodiment, the current detector 122 starts detection of current flowing in the common electrode lines 95. The controller 106 considers that radiation irradiation has started in a case in which the detected current value is the detection threshold value or greater. During detection of current flowing in the common electrode lines 95, current flowing in the common electrode lines 95 may be detected with the TFT switches 74 of each of the pixels 100 in placed an OFF state. Or, the current flowing in the common electrode lines 95 may be detected with the TFT switches 74 temporarily placed in an ON state. At the next step S106, transition is made to the charge accumulation state (accumulation period), and charge accumulation starts at step S108.

At the next step S110, determination is made as to whether or not noise has occurred. As described above, in the present exemplary embodiment, the controller 106 detects the occurrence of noise based on the current value detected by the current detector 122. In a case in which noise occurrence is detected, affirmative determination is made, and processing returns to step S102 following step S112 and step S114, similarly to in the first exemplary embodiment.

In a case in which noise has not occurred, negative determination is made, processing continues to step S118, and the present routine is ended following step S120 and step S122, similarly to in the first exemplary embodiment.

In the present exemplary embodiment, the current flowing in the common electrode lines 95 is detected by the current detector 122, and the controller 106 determines whether or not the change with time of the current value has the predetermined characteristics of noise. In a case in which the characteristics are present, noise is determined to have occurred, operation of the electronic cassette 20 is stopped, the charge accumulation period is interrupted (ceased), and transition is made to the radiation detection period.

Accordingly, based on the current value of the current flowing in the common electrode lines 95 during the charge accumulation period, detection of whether or not noise caused by external disturbance has occurred is enabled similarly to in the first exemplary embodiment. Further, driving of the electronic cassette 20 is stopped immediately in the case in which the occurrence of noise has been detected. In this way, since it is possible to detect noise and control the imaging operation of the electronic cassette 20 without any delay in cases in which noise caused by external disturbance has occurred, the time from noise occurrence detection to re-imaging can be shortened. This thereby enables unnecessary exposure to the subject 30 (ineffective exposure that does not contribute to generation of a radiographic image) to be reduced.

In the above explanation, explanation has been given regarding a case in which current flowing in the common electrode lines 95 is detected by the current detector 122; however, there is no limitation thereto. As illustrated in FIG. 14A, the detection method may, for example, be configured by accumulating charges flowing in the common electrode lines 95 in a charge accumulation section 128, and detecting noise occurrence and radiation irradiation start based on the accumulated charges. The detection method may also, as for example illustrated in FIG. 14B, be configured by detecting the voltage of the current flowing in the common electrode lines 95 using a voltage detector 126, and detecting noise occurrence and radiation irradiation start based on the detected voltage value.

In the above explanation, explanation has been given regarding a case in which noise occurrence and radiation irradiation start are detected based on the current flowing in all of the common electrode lines 95. However, there is no limitation thereto, and noise occurrence and radiation irradiation start may be detected based on the current flowing in some of the common electrode lines 95.

In the present exemplary embodiment, explanation has been given regarding a case in which radiation irradiation start is detected together with detection of noise caused by external disturbance, based on charges or the like flowing in the common electrode lines. However, there is no limitation thereto, and a current detector 122 similarly to the present exemplary embodiment may be provided inside the scan signal control circuit 104, and, similarly to in the above explanation, noise occurrence and radiation irradiation start may be detected based on changes in the current flowing in the gate lines 101. Moreover, for example, a current detector 122 similarly to in the present exemplary embodiment may be provided inside the signal detection circuit 105, and, similarly to in the above explanation, noise occurrence and radiation irradiation start may be detected based on changes in the current flowing in the signal lines 73.

Third Exemplary Embodiment

Figure 15:
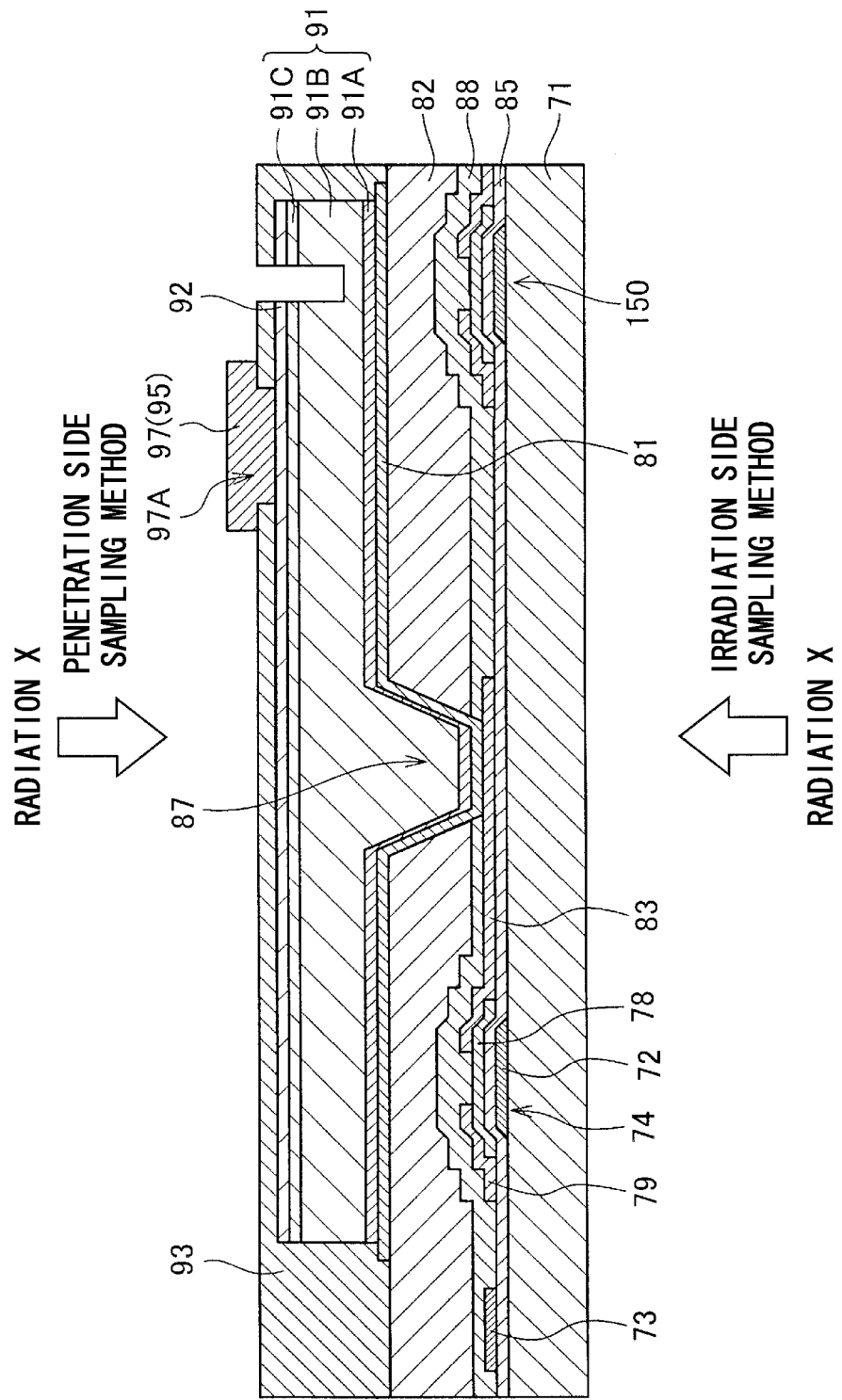
FIG. 15 is a line cross-section illustrating an example of a radiation detector according to a third exemplary embodiment.

The configuration for detecting noise occurrence and radiation irradiation start based on changes in the electrical signals due to charges generated in the pixels 100 is not limited to the respective exemplary embodiments described above. For example, as illustrated in FIG. 15, second sensor portions 150 for radiation detection may be provided. In such cases, the second sensor portions 150 are preferably provided between the pixels 100.

Charges are generated in the second sensor portions 150 for radiation detection in cases in which radiation is irradiated, and in cases in which noise caused by external disturbance occurs. These charges have similar properties to the charges generated in the sensor portions 103 of the pixels 100 in the respective exemplary embodiments described above.

Source electrodes and gate electrodes of the second sensor portions 150 for radiation detection are respectively connected to the controller 106. In the controller 106, noise occurrence and radiation irradiation start are detected similarly to in each of the exemplary embodiments described above, based on changes in electrical signals caused by charges flowing from the second sensor portions 150 for radiation detection.

Accordingly, similarly to in the respective exemplary embodiments described above, this configuration also enables detection of whether or not noise caused by external disturbance has occurred, based on charges generated in the second sensor portions 150 for radiation detection during the charge accumulation period. Driving of the electronic cassette 20 is stopped immediately in the case in which the occurrence of noise has been detected. Thus, since it is possible to detect noise occurrence and control the imaging operation of the electronic cassette 20 without any delay in cases in which noise caused by external disturbance has occurred, the time from noise occurrence detection to re-imaging can be shortened. This thereby enables unnecessary exposure to the subject 30 (ineffective exposure that does not contribute to generation of a radiographic image) to be reduced.

Fourth Exemplary Embodiment

Figure 16A:
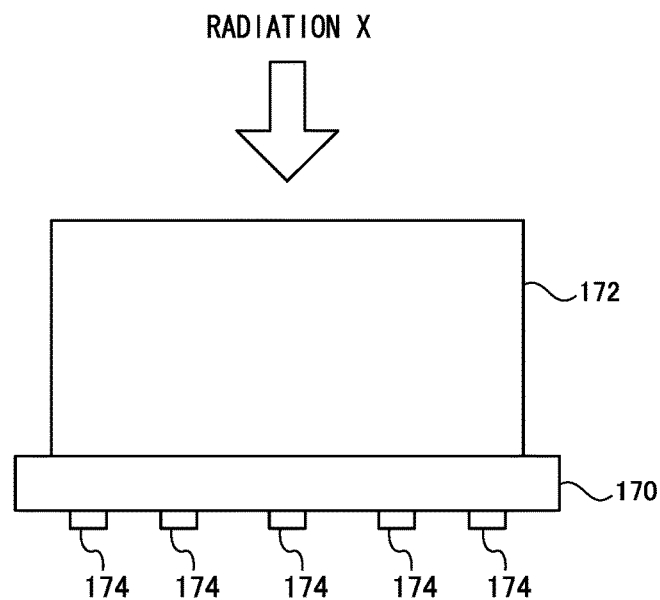
FIG. 16A is a schematic configuration diagram shown in side view, illustrating an example of a case in which sensors according to a fourth exemplary embodiment are externally provided to a radiation detector.
Figure 16B:
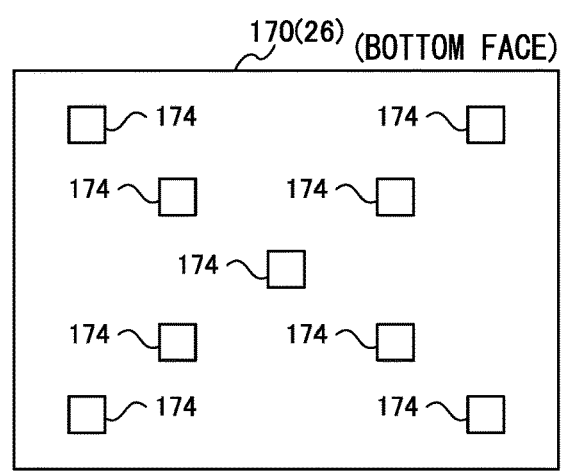
FIG. 16B is a schematic configuration diagram shown in plan view from a bottom side, illustrating an example of a case in which sensors according to the fourth exemplary embodiment are externally provided to the radiation detector, as illustrated in FIG. 16A.

In each of the exemplary embodiments described above, explanation has been given regarding cases in which radiation irradiation start and noise occurrence are detected by sensors or the like provided within the radiation detector 26; however, there is no limitation thereto. As described above, radiation irradiation start and noise occurrence may be detected by sensors provided externally to the radiation detector 26. FIG. 16A and FIG. 16B are schematic drawings illustrating a case in which sensors are provided externally to the radiation detector 26.

In the example illustrated in FIG. 16A, the radiation detector 26 is irradiated with radiation X from a side of a TFT substrate 170 provided with pixels 100 on which a scintillator 172 is disposed. Radiation detection sensors 174 are disposed on the radiation X non-irradiated side on which the scintillator 172 is not disposed, which is the bottom face of the TFT substrate 170 (radiation detector 26). In the present exemplary embodiment, by way of a specific example, nine radiation detection sensors 174 are provided, as illustrated in FIG. 16B.

The radiation detection sensors 174 are not particularly limited, as long as they output electrical signals according to an amount of irradiated radiation X. In the present exemplary embodiment, silicon sensors including Si (silicon) photodiodes are used as the radiation detection sensors 174 by way of a specific example. Electromagnetic shielding is preferably applied to the radiation detection sensors 174.

As radiation X passes through the radiation detection sensors 174 configured by silicon sensors, ionizing action splits atoms in the radiation detection sensors 174 into cations and electrons and a minute current flows as they respectively move toward the negative electrode side and the positive electrode side. The controller 106 detects electrical signals according to this current, and noise occurrence and radiation irradiation start are detected, similarly to in the each of the exemplary embodiments described above, based on changes in these electrical signals.

For example, processing is performed that is substantially the same as that of the flowchart in FIG. 9 illustrating an example of a flow of operation during radiographic imaging.

Having transitioned to the imaging mode, the controller 106 detects the electrical signals output from the plural radiation detection sensors 174 during the radiation detection period. The controller 106 detects radiation irradiation start by determining whether or not the electrical signals satisfy a preset condition for radiation irradiation start as described above. Here, radiation irradiation may be determined to have started in cases in which the detected electrical signals from one or more out of the plural radiation detection sensors 174 satisfy the preset condition. The number of the radiation detection sensors 174 that must satisfy the preset condition in order to determine radiation irradiation to have started is not limited thereto, and may be set to be a specific number of individuals or greater, or may be set as all of the radiation detection sensors 174. Settings may also be made according to the placement locations of the radiation detection sensors 174.

After radiation irradiation start has been detected, the controller 106 uses the scan signal control circuit 104 to place the gates of the TFT switches 74 of the radiation detector 26 in the OFF state, and transition is made to the accumulation period to accumulate charges generated in the sensor portions 103 due to irradiation with the radiation X. In cases in which the gates are placed in an OFF state, the gates of the TFT switches 74 of all of the pixels 100 may be placed in the OFF state all at once.

In the present exemplary embodiment, the radiation detection sensors 174 continue to detect electrical signals even after transition has been made to the accumulation period following detection of the radiation irradiation start. The controller 106 detects the occurrence of noise by determining whether or not the electrical signals mentioned above satisfy the preset condition for detecting noise occurrence. In a case in which occurrence of noise has been detected, charge accumulation is stopped and notification is made that noise has occurred. The controller 106 also performs a reset operation, and after the resetting the charges accumulated in the sensor portions 103, processing returns to the radiation detection period, and radiation irradiation start detection is performed again.

In a case in which noise has not occurred, detection of the electrical signals from the radiation detection sensors 174 is ended at the stage when transition is made from the accumulation period to the reading period for reading the accumulated charges.

Thus, detection of whether or not noise caused by external disturbance has occurred can be made based on the electrical signals (current) from the radiation detection sensors 174 during the charge accumulation period, similarly to in each of the exemplary embodiments described above, even in cases in which the sensors (the radiation detection sensors 174) are provided externally to the radiation detector 26. Further, noise occurrence can be detected and the imaging operation (current operation) of the electronic cassette 20 can be controlled, without any delay, in cases in which noise caused by external disturbance has occurred.

Note that the number and placement of the radiation detection sensors 174 is not limited to that of the present exemplary embodiment. The radiation detection sensors 174 are preferably disposed at a central portion of the TFT substrate 170 so as to enable appropriate detection of the radiation X even in cases in which the irradiation range has been narrowed. The radiation detection sensors 174 may also be disposed at different densities at a central portion and at peripheral portions. For example, higher density placement may be made at a central portion than at peripheral portions.

Note that in each of the exemplary embodiments described above, explanation has been given regarding cases in which the same detection methods (refer to methods (1) to (6) described above) are used to detect noise occurrence and to detect radiation irradiation start; however, there is no limitation thereto. The detection method (the method of the embodiments) for radiation irradiation start and the detection method for noise occurrence may be different from each other, and for example, the type of electrical signals (for example, leak current, or bias current) used for detecting radiation irradiation start and the electrical signals used for detecting noise occurrence may be different from each other.

For example, the respective exemplary embodiments described above may be combined. By way of a specific example, radiation irradiation start detection may use any one of the first exemplary embodiment to the third exemplary embodiment, and the noise occurrence detection may use the fourth exemplary embodiment. In such cases, the controller 106 performs radiation irradiation start detection and noise occurrence detection at the same time. In such cases, noise occurrence detection is performed using only the radiation detection sensors 174 illustrated in the fourth exemplary embodiment. Cases in which current is not detected (electrical signals are not detected) by the radiation detection sensors 174 even though radiation irradiation start had been detected mean that radiation irradiation start had been detected even though the radiation X is not actually being irradiated, and so noise is determined to have occurred. In a case in which noise occurrence has been detected, as described above, charge accumulation is stopped and after resetting the accumulated charges, processing once again returns to the radiation detection period, and radiation irradiation start detection is performed.

In another example, configuration may be made such that any of the first exemplary embodiment, the third exemplary embodiment, or the fourth exemplary embodiment is used in radiation irradiation start detection, and the second exemplary embodiment is used in noise occurrence detection. Once again, in such cases the controller 106 performs radiation irradiation start detection and noise occurrence detection at the same time. In such cases, noise occurrence detection is performed based on charges (electrical signals)

flowing in the common electrode lines 95, as illustrated in the second exemplary embodiment. Cases in which charges do not flow in the common electrode lines 95 (or cases in which charges do flow, but noise occurrence has been detected) even though radiation irradiation start had been detected mean that radiation irradiation start had been detected even though radiation X is not actually being irradiated, and so noise is determined to have occurred. In a case in which noise occurrence has been detected, charge accumulation is stopped and after resetting the accumulated charges, processing once again returns to the radiation detection period, and radiation irradiation start detection is performed.

Obviously, each of the exemplary embodiments described above may be combined. For example, radiation irradiation start detection, and noise occurrence detection, may respectively be performed using plural detection methods.

Figure 17:
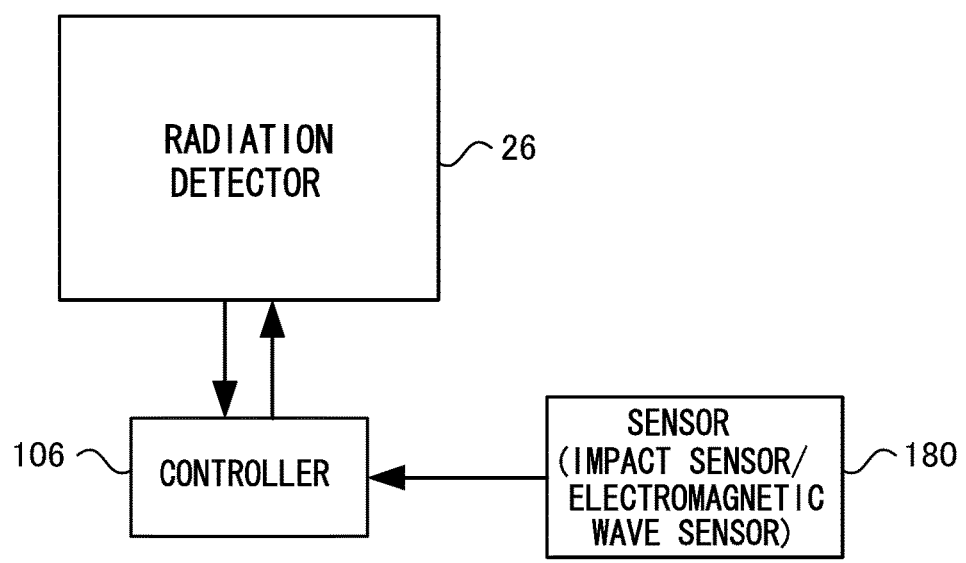
FIG. 17 is a schematic configuration diagram of an example of a case in which an impact sensor that detects impacts directly, or an electromagnetic wave sensor that detects electromagnetic waves, is provided to detect the occurrence of noise.

Moreover, noise occurrence detection is not limited to the respective exemplary embodiments described above, and impact sensors that detect impacts directly, and electromagnetic wave sensors that detect electromagnetic waves may, for example, be used. FIG. 17 is a schematic configuration diagram illustrating an example of a case in which such sensors are used.

A sensor 180 is an impact sensor, or an electromagnetic wave sensor. For example, in a case in which the sensor 180 detects that an impact to the radiation detector 26 has occurred, a signal notifying impact occurrence is output to the controller 106. On receipt of the impact occurrence notification, the controller 106 detects that noise has occurred, and charge accumulation is stopped as described above. After resetting the accumulated charges, processing once again returns to the radiation detection period, and radiation irradiation start detection is performed.

An acceleration sensor or the like is a specific example of an impact sensor that may configure the sensor 180. In cases of using an impact sensor, electromagnetic shielding is preferably applied to the impact sensor.

The sensor 180 may be provided inside the electronic cassette 20, or may be provided externally to the electronic cassette 20 (for example, to a side face of the electronic cassette 20).

Note that in each of the exemplary embodiments described above, explanation has been given regarding cases in which noise occurrence detection is performed during the charge accumulation period. However, there is no limitation thereto, and noise occurrence detection may be performed during the reading period. In such cases, in a case in which noise occurrence is detected, the read operation is interrupted (ceased) and transition is made to the radiation detection period. Noise occurrence may also be detected prior to the start of the charge accumulation period. Explanation follows regarding the fifth exemplary embodiment and the sixth exemplary embodiment for cases in which noise occurrence is detected prior to the start of the charge accumulation period.

Fifth Exemplary Embodiment

Figure 18:
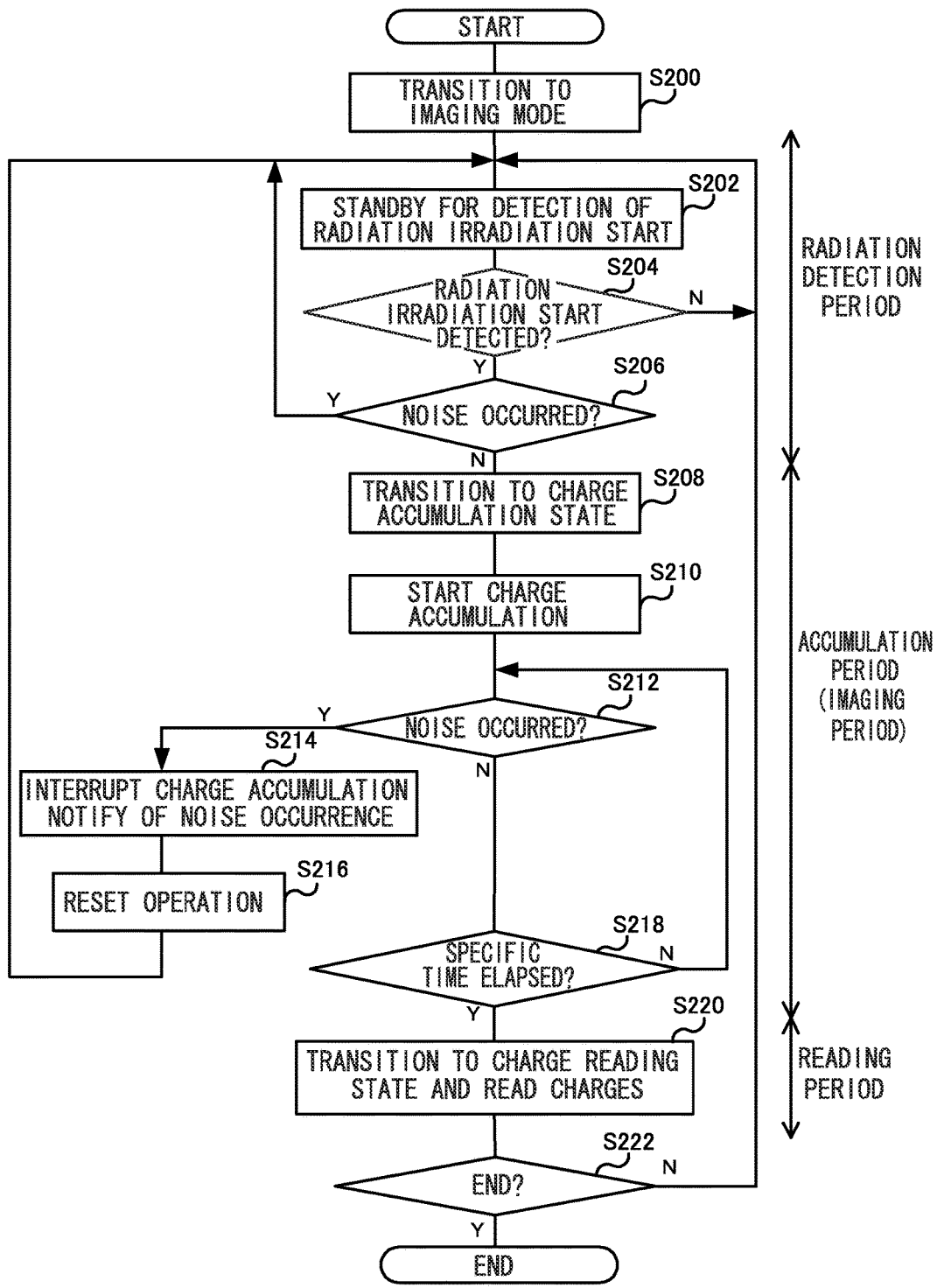
FIG. 18 is a flowchart illustrating an example of a flow of operation in radiographic imaging according to a fifth exemplary embodiment.

In the present exemplary embodiment, explanation is given regarding a case in which noise occurrence is detected during the charge accumulation period and prior to the charge accumulation period. FIG. 18 is a flowchart illustrating an example of a flow of operation during radiographic imaging according to the present exemplary embodiment. The present operation includes operation substantially the same as the operation during radiographic imaging explained with respect to each to exemplary embodiments described above (see FIG. 9). In particular, in the present operation, a noise occurrence detection operation during the charge accumulation period is substantially the same as the noise occurrence detection operation during the charge accumulation period explained with respect to the respective exemplary embodiments described above. Therefore, operation that is substantially the same is indicated as such, and detailed explanation thereof is omitted.

Step S200 to step S204 of operation during radiographic imaging in the present exemplary embodiment respectively correspond to the operation of step S100 to step S104 described above.

After transitioning to the imaging mode at step S200, at the next step S202 transition is made to a radiation detection standby state in which detection is made for radiation. At the next step S204, determination is made as to whether or not radiation irradiation start has been detected. In a case of no detection, negative determination is made, processing returns to step S202 and the present processing is repeated.

In a case in which radiation irradiation start has been detected, affirmative determination is made and transition is made to step S206. At step S206, determination is made as to whether or not noise has occurred. The noise occurrence detection method (algorithm) at step S206 is not particularly limited. The noise occurrence detection method may be the same as that explained in the exemplary embodiments above.

Figure 19:
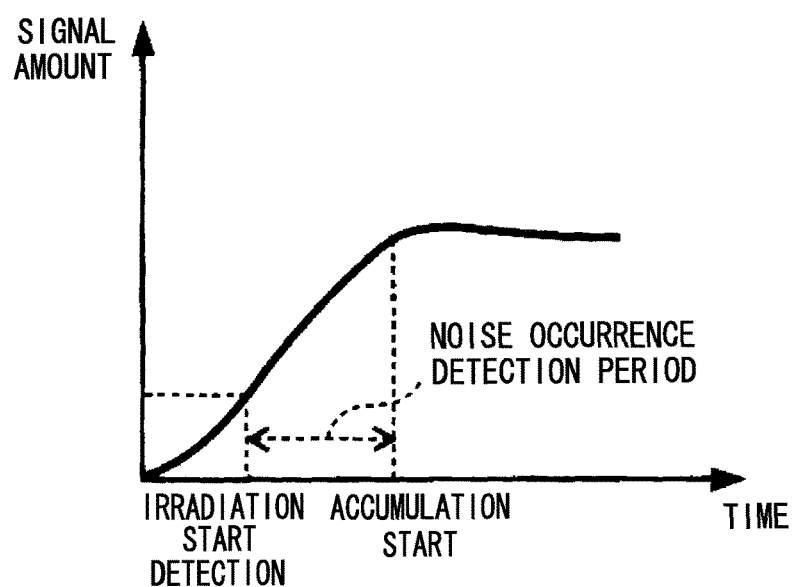
FIG. 19 is an explanatory drawing illustrating an example of a relationship between time and signal amount (an electrical signal amount of radiation that has been converted into charge) in cases in which the occurrence of noise is only detected prior to a charge accumulation period.
Figure 20:
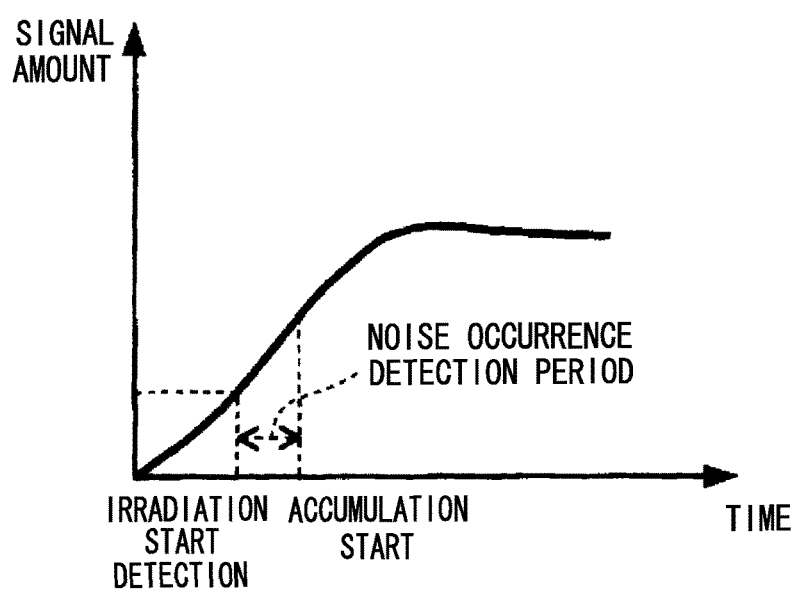
FIG. 20 is an explanatory drawing illustrating an example of a relationship between time and signal amount in a case (such as in the present exemplary embodiment) in which noise occurrence detection is performed prior to a charge accumulation period and during the charge accumulation period.

Generally, in a case in which noise occurrence detection is only performed prior to the charge accumulation period then noise occurrence detection takes longer than in a case in which noise occurrence is also detected after the start of the charge accumulation period as in the present exemplary embodiment. FIG. 19 illustrates an example of a relationship between time and signal amount (the electrical signal amount of radiation that has been converted into charges) in cases in which noise occurrence detection is only performed prior to the charge accumulation period. FIG. 20 illustrates an example of a relationship between time and signal amount in cases in which noise occurrence detection is performed prior to the charge accumulation period and during the charge accumulation period (the present exemplary embodiment).

In cases in which noise occurrence detection is only performed prior to the charge accumulation period, in order to perform appropriate noise occurrence detection, it is necessary to extend the specific detection period for electrical signal sampling (the noise occurrence detection period). For example, in the example illustrated in FIG. 19, since there is a monotonic increase in the signal amount in the noise occurrence detection period, determination is made that noise has not occurred.

However, in cases in which, as in the present exemplary embodiment, noise occurrence detection is performed prior to the charge accumulation period and during the charge accumulation period, the noise occurrence detection prior to the charge accumulation period may need not be perfect since noise occurrence detection is also performed during the charge accumulation period. Accordingly, as illustrated in FIG. 20, the noise occurrence detection period may be shorter than in the example illustrated in FIG. 19. Even with a short noise occurrence detection period, noise with a short cycle (see FIG. 8) may be detected since the signal amount thereof does not increase monotonically.

Accordingly, in the present exemplary embodiment, the noise occurrence detection period can be made shorter in cases in which detection of short cycle noise occurrence is performed prior to the charge accumulation period.

Note that the noise detection algorithm differs depending on what sort of noise is being targeted. The noise detection algorithm also differs depending on the specifications of the radiographic imaging system 10 and the electronic cassette 20, user preference, and the like. Therefore, it is preferable that the noise detection algorithm is configurable according to imaging conditions, for example, using an imaging menu, user instruction or the like.

In a case in which noise occurrence has been detected, determination is affirmative at step S206 and processing returns to step S202. In cases in which noise occurrence has not been detected, determination is negative and processing proceeds to step S208. Step S208 to step S222 respectively correspond to the operation of step S106 to step S122 described above, and explanation thereof is omitted.

In this way in the present exemplary embodiment, noise occurrence detection is performed prior to the charge accumulation period, and during the charge accumulation period. The present exemplary embodiment can accordingly detect noise occurrence without any delay and control the imaging operation (current operation) of the electronic cassette 20 in cases in which noise caused by external disturbance has occurred.

In practice, false detection of radiation irradiation start leading to transition to the charge accumulation period even though radiation irradiation has not started occurs frequently in noisy environments in cases in which noise detection is performed after starting the charge accumulation period, as explained in the respective exemplary embodiments above. There are therefore concerns of an increase in power consumption. However, in the present exemplary embodiment, noise occurrence detection is performed prior to the transition to the charge accumulation period. Therefore, transition to the charge accumulation period can be prevented, enabling an increase in power consumption to be reduced.

In cases in which noise detection is only performed prior to the charge accumulation period, high speed detection cannot be performed since a long time is required for the noise occurrence detection period, as described above. There is also an increase in discarded charges (charges that are not employed in radiographic image generation and are discarded). Since a specific amount of charges are required for radiographic image generation, an increase in discarded charges increases the time for obtaining the specific amount of charges. Namely, the irradiation time increases, and the amount of irradiated radiation increases. In contrast, in the present exemplary embodiment, the noise occurrence detection period can be made shorter, as described above. High speed detection can accordingly be performed. The amount of discarded charges can also be reduced.

Sixth Exemplary Embodiment

In the present exemplary embodiment, explanation is given regarding a case in which noise occurrence is detected prior to the charge accumulation period and after the charge accumulation period has ended. FIG. 21 is a flowchart illustrating an example of a flow of operation during radiographic imaging according to the present exemplary embodiment. The present operation includes operation substantially the same as the operation during radiographic imaging described in the respective exemplary embodiments above (see FIG. 9 and FIG. 18). In particular, the noise occurrence detection operation prior to the charge accumulation period is substantially the same as the noise occurrence detection operation prior to the charge accumulation period explained in the fifth exemplary embodiment above. Therefore, operation that is substantially the same is indicated as such, and detailed explanation thereof is omitted.

Step S300 to step S310 of the operation during radiographic imaging in the present exemplary embodiment respectively correspond to the operation of step S200 to step S210 of the fifth exemplary embodiment (see FIG. 18).

After transition to the imaging mode at step S300, at the next step S302 transition is made to the radiation detection standby state in which detection is made for radiation. At the next step S304, determination is made as to whether or not radiation irradiation start has been detected. In a case of no detection, negative determination is made, processing returns to step S302 and the present processing is repeated. In a case in which radiation irradiation start has been detected, processing transitions to step S306, and determination is made as to whether or not noise has occurred. In a case in which noise occurrence has been detected, processing returns to step S302. In a case in which noise occurrence has not been detected, processing proceeds to step S308, transition is made to a charge accumulation state, and charge accumulation is started at the next step S310.

In the present exemplary embodiment, at the next step S312 determination is made as to whether or not a specific time for charge accumulation has elapsed since starting charge accumulation at step S310. Step S312 corresponds to step S118 or step S218 in the exemplary embodiments described above. Determination is negative and a standby state continues until the specific time has elapsed. Once the specific time has elapsed, determination is affirmative and processing proceeds to step S314.

After the specific time has elapsed and charge accumulation has been completed, at step S314 determination is made as to whether or not noise has occurred. The noise occurrence detection method (algorithm) at step S314 is not particularly limited. The noise occurrence detection method may be the same as that described in the exemplary embodiments above. Processing proceeds to step S316 in the case in which noise occurrence has been detected. At step S316, the user, for example a doctor, is notified that noise has occurred similarly to the noise occurrence notification at step S112 in the exemplary embodiments described above, after which processing proceeds to step S320. In the case in which noise occurrence has not been detected, processing transitions to step S318. Step S318 and step S320 respectively correspond to the operation of step S120 to step S122 (step S220 and step S222) described above, and explanation thereof is omitted.

In this way, in the present exemplary embodiment, noise occurrence detection is performed prior to the charge accumulation period and after the charge accumulation period has ended. Similarly to in the respective exemplary embodiments described above, in a case in which noise caused by external disturbance occurs, the noise occurrence can be detected and the imaging operation (current operation) of the electronic cassette 20 can be controlled without any delay.

In cases in which noise occurrence detection is only performed prior to the charge accumulation period, noise is incorporated into the generated radiographic image if noise occurs after detection. Moreover, as described in the respective exemplary embodiments above, depending on the detection timing, there is a concern of being unable to perform appropriate noise occurrence detection even in cases in which noise occurrence detection is performed during the charge accumulation period. For example, there is a concern of not being able to detect noise occurring nearly at the end of the charge accumulation period. Therefore, the respective exemplary embodiments described above may not provide guarantee that noise will not be incorporated into a generated radiographic image. In contrast, in the present exemplary embodiment, noise occurrence detection is performed before the charge accumulation period and after the end of the charge accumulation period. In a case in which noise is not detected in either case, it may be assumed that noise did not occur during the charge accumulation period either. The present exemplary embodiment accordingly enables to prevent the incorporation of noise into radiographic images.

In the present exemplary embodiment, notification is made in a case in which noise occurrence is detected after the charge accumulation period has ended. However, notification may also be made not only of the occurrence of noise, but also of the strength and occurrence position of the noise that occurred. In such cases, the strength of the noise that occurred may be detected based on the strength of the electrical signals used in the noise detection, for example. The noise occurrence position may also be detected based on the position of the sensor(s) (radiation sensor(s)) that has detected the electrical signals for noise occurrence detection.

Moreover, determination as to whether or not to generate a radiographic image (or whether or not to output a generated radiographic image) may be made according to the strength and occurrence position of the detected noise. For example, configuration may be made such that a radiographic image is generated in a case in which the noise that occurred is weak, and a radiographic image is not generated in a case in which the noise that occurred is strong. Alternatively, for example, configuration may be made such that a radiographic image is generated in a case in which the noise occurrence position is at a peripheral portion of the image, and a radiographic image is not generated in a case in which the noise that occurred is in the vicinity of a central portion, or is in a region showing an imaging subject.

In the present exemplary embodiment, noise occurrence is detected after charge accumulation has ended, after which transition is made to the charge reading state; however, there is no limitation thereto. For example, noise occurrence detection may be performed parallel to charge reading. In cases in which noise occurrence detection is performed parallel to charge reading, radiation is also irradiated onto the electronic cassette 20 during charge reading. Therefore, it is preferable to provide a shield portion (shutter), for example, such that the sensors (radiation sensors) that detect electrical signals for noise occurrence detection are irradiated with radiation, and the pixels 100 from which charge is read to generate a radiographic image are not irradiated with radiation, or irradiation is reduced.

Note that in cases in which noise detection is performed after starting the charge accumulation period as explained in the first exemplary embodiment to the fourth exemplary embodiment above, there is a concern that the issue mentioned in the fifth exemplary embodiment might arise in noisy environments. Namely, there is a concern of an increase in power consumption due to frequent occurrence of false detection of radiation irradiation start, leading to transition to the charge accumulation period even though radiation irradiation has not started. For example, imaging is performed in noisy environments in cases in which radiographic imaging is performed during a doctor's rounds. In such cases, unlike in a radiographic imaging room, measures against electromagnetic noise may not necessarily in place, and there may be a lot of noise from nearby machinery. Moreover, in hospital wards, since beds are lined up in rows and space is tight, contact between cables and beds leads to an increase in impact noise. When performing imaging in such noisy environments, the electronic cassette 20 is preferably used fitted with a protective casing cover such as a jacket (external reinforcement casing). This enables unnecessary transition to the accumulation period to be prevented and enables power consumption to be reduced, even in noisy environments.

Note that in the respective exemplary embodiments described above, explanation has been given regarding cases in which the present invention is applied to the indirect conversion type radiation detector 26 that converts converted light into charges; however, there is no limitation thereto. For example, the present invention may be applied to a direct conversion type radiation detector using a material such as amorphous selenium that converts radiation directly into charges in a photoelectric conversion layer that absorbs radiation and converts the radiation into charges.

Other configuration and operation of the electronic cassette 20, the radiation detector 26, and so on explained in the present exemplary embodiment are merely examples thereof, and obviously modifications may be made as circumstances dictate within a range not departing from the spirit of the present invention.

The radiation of the present invention is not particularly limited to the present exemplary embodiment, and X-rays or gamma rays may be applied.

All publications, patent applications and technical standards mentioned in the present specification are incorporated by reference in the present specification to the same extent as if the individual publication, patent application, or technical standard was specifically and individually indicated to be incorporated by reference.

What is claimed is:

1. A radiographic imaging device comprising:
   a radiation detector including a plurality of pixels, each including a sensor portion that generates charges according to an amount of irradiated radiation and accumulates the generated charges;
   a detection unit that performs a detection operation that detects a radiation irradiation start in at least one of a case in which an electrical signal caused by charges generated in the sensor portion that serves as a radiation sensor portion for detecting radiation irradiation start satisfies a specific irradiation detection condition, or a case in which an electrical signal caused by charges generated in a radiation sensor portion for detecting radiation irradiation start that is different from the sensor portion satisfies a specific irradiation detection condition; and
   a control unit that, after the detection unit has detected the radiation irradiation start, determines whether or not noise caused by external disturbance has occurred based on changes in an electrical signal output from any one of the radiation sensor portion, an impact sensor or an electromagnetic wave sensor for detecting radiation irradiation start, and in a case in which it has been detected that the noise has occurred, that causes the detection unit that has been stopped the detection operation to restart the detection operation.

2. The radiographic imaging device of claim 1, wherein the control unit causes, in the case in which it has been detected that the noise has occurred, the detection unit to restart the detection operation after resetting the sensor portion.

3. The radiographic imaging device of claim 1, wherein the control unit causes, in the case in which it has been detected that the noise has occurred, the sensor portion to terminate the charge accumulation by interrupting the charge accumulation in the sensor portion.

4. The radiographic imaging device of claim 1, wherein after the detection unit has detected radiation irradiation start and before performing charge accumulation in the sensor portions, the control unit determines whether or not the noise has occurred, and causes the sensor portions to start the charge accumulation in a case in which the noise has not occurred.

5. The radiographic imaging device of claim 1, wherein each of the plurality of pixels further comprises a switching element that reads the charges from the sensor portion and outputs electrical signals according to the charges into a signal line, the plurality of pixels comprises at least one shorted pixel in which the switching element has been shorted; and
the control unit determines whether or not the noise has occurred based on change in an electrical signal output from the sensor portion of the shorted pixel.

6. The radiographic imaging device of claim 1, further comprising a common electrode line that supplies a bias voltage to the sensor portions;
wherein the control unit determines whether or not the noise has occurred based on change in an electrical signal output from the sensor portions and flowing in the common electrode line.

7. The radiographic imaging device of claim 1, wherein the electrical signal represents leak current in selected pixels among the plurality of pixels.

8. The radiographic imaging device of claim 1, wherein the radiation sensor portion is provided at least one of internally or externally to the radiation detector; and
the control unit determines whether or not the noise has occurred based on change in an electrical signal output from the radiation sensor portion.

9. The radiographic imaging device of claim 8, wherein the radiation sensor portion is applied with electromagnetic shielding.

10. The radiographic imaging device of claim 8, further comprising a plurality of the radiation sensor portions, wherein the radiation detection sensors are disposed at different densities at a central portion and at peripheral portions of an incident face of radiation of the radiation detector.

11. The radiographic imaging device of claim 1, wherein the control unit determines whether or not the noise has occurred based on change in at least one of polarity of charges according to an electrical signal, or the amplitude of a waveform representing change with time of a charge amount according to an electrical signal.

12. The radiographic imaging device of claim 1, wherein an electrical signal with which the detection unit detects radiation irradiation start, and an electrical signal with which the control unit determines whether or not the noise has occurred, are different types of electrical signals from each other.

13. The radiographic imaging device of claim 1, wherein the control unit determines whether or not the noise has occurred using at least one of a predetermined criterion for each specific region where the pixels are provided, or a predetermined criterion for each of signal lines to which charges read from the sensor portion are output.

14. The radiographic imaging device of claim 1, wherein each of the plurality of pixels further comprises a switching element that reads the charges from the sensor portion and outputs electrical signals according to the charges into a signal line, the plurality of pixels comprises at least one shorted pixel in which the switching element has been shorted; and
the detection unit detects the radiation irradiation start in a case in which an electrical signal output from the sensor portion of the shorted pixel satisfies a specific irradiation detection condition.

15. The radiographic imaging device of claim 1, further comprising a common electrode line that supplies a bias voltage to the sensor portions;
wherein the detection unit detects the radiation irradiation start in a case in which an electrical signal output from the sensor portions and flowing in the common electrode line satisfies a specific irradiation detection condition.

16. The radiographic imaging device of claim 1, wherein the radiation sensor portion is provided at least one of internally or externally to the radiation detector; and
the detection unit detects as radiation irradiation start in a case in which an electrical signal output from the radiation sensor portion satisfies a specific irradiation detection condition.

17. The radiographic imaging device of claim 1, further comprising a notification unit that provide notification to a user in the case in which noise has occurred.

18. The radiographic imaging device of claim 1, wherein the electrical signal represents current or voltage.

19. The radiographic imaging device of claim 1, wherein the detection operation comprises electrical signal sampling.

20. The radiographic imaging device of claim 1, wherein the electrical signal is output from a plurality of sensors selected from the radiation sensor portion, the impact sensor or the electromagnetic wave sensor.

21. A radiographic imaging system comprising:
an irradiation device that irradiates radiation; and
the radiographic imaging device of claim 1, that captures a radiographic image according to radiation irradiated from the irradiation device.

22. A non-transitory storage medium storing a control program that causes a radiographic imaging device to perform control processing, the radiographic imaging device including a radiation detector including a plurality of pixels, each including a sensor portion that generates charges according to an amount of irradiated radiation and accumulates the generated charges, the control processing comprising:
performing detection operation of a radiation irradiation start by at least one of: (a) detecting an electrical signal caused by charges generated in the sensor portion that serves as a radiation sensor portion for detecting radiation irradiation start satisfying a specific irradiation detection condition, or (b) detecting an electrical signal caused by charges generated in a radiation sensor portion for detecting radiation irradiation start that is different from the sensor portion satisfying a specific irradiation detection condition;
after the radiation irradiation start has been detected, determining whether or not noise caused by external disturbance has occurred based on changes in an electrical signal output from any one of the radiation sensor portion, an impact sensor or an electromagnetic wave sensor for detecting radiation irradiation start; and
in a case in which it has been detected that the noise has occurred, causing the radiation detector that has been stopped the detection operation to restart the detection operation.

23. A control method for a radiographic imaging device comprising a radiation detector including a plurality of pixels, each including a sensor portion that generates charges according to an amount of irradiated radiation and accumulates the generated charges, the radiographic imaging device control method comprising:
   performing detection operation of a radiation irradiation start by at least one of: (a) detecting an electrical signal caused by charges generated in the sensor portion that serves as a radiation sensor portion for detecting radiation irradiation start satisfying a specific irradiation detection condition, or (b) detecting an electrical signal caused by charges generated in a radiation sensor portion for detecting radiation irradiation start that is different to the sensor portion satisfying a specific irradiation detection condition;
   after the radiation irradiation start has been detected, determining whether or not noise caused by external disturbance has occurred based on changes in an electrical signal output from any one of the radiation sensor portion, an impact sensor or an electromagnetic wave sensor for detecting radiation irradiation start; and
   in a case in which it has been detected that the noise has occurred, causing the radiation detector that has been stopped the detection operation to restart the detection operation.

* * * * *